United States Patent [19]

Hyzak et al.

[11] Patent Number: 4,915,725

[45] Date of Patent: Apr. 10, 1990

[54] HERBICIDE COMPOSITIONS OF EXTENDED SOIL LIFE

[75] Inventors: Daniel L. Hyzak, Austin, Tex.; Reed A. Gray, Saratoga, Calif.

[73] Assignee: ICI Americas, Inc., Wilmington, Del.

[21] Appl. No.: 605,441

[22] Filed: Apr. 30, 1984

Related U.S. Application Data

[63] Continuation-in-part of Ser. No. 507,616, Jun. 24, 1983, abandoned, which is a continuation-in-part of Ser. No. 304,216, Sep. 21, 1981, abandoned, which is a continuation-in-part of Ser. No. 198,034, Oct. 17, 1980, abandoned, which is a continuation of Ser. No. 60,603, Jul. 27, 1979, abandoned, which is a continuation-in-part of Ser. No. 944,094, Sep. 20, 1978, abandoned.

[51] Int. Cl.$^4$ .............................................. A01N 57/02
[52] U.S. Cl. .................................. 71/87; 71/88; 71/90; 71/91; 71/100
[58] Field of Search ..................................... 71/87, 100

[56] References Cited

U.S. PATENT DOCUMENTS

| | | | |
|---|---|---|---|
| 2,913,327 | 11/1959 | Tilles et al. | 71/100 |
| 3,492,376 | 1/1970 | Beriger et al. | 424/225 |
| 3,932,632 | 1/1976 | Adolphi et al. | 424/213 |
| 3,938,986 | 2/1976 | Pray | 71/100 |
| 4,004,001 | 1/1977 | Large et al. | 424/200 |
| 4,035,490 | 7/1977 | Pitt | 424/225 |
| 4,047,928 | 9/1977 | Bond et al. | 71/107 |
| 4,123,526 | 10/1978 | Large et al. | 424/200 |
| 4,507,143 | 3/1985 | Schafer et al. | 71/87 |

FOREIGN PATENT DOCUMENTS 964793  7/1964  United Kingdom ................ 71/86

OTHER PUBLICATIONS

Byers et al., "Systemic Insecticides, etc.", (1977) CA 87 No. 128777X, (1977).
Nash, "Synergistic Phytotoxicities, etc.", (1967) Weed Science 16, No. 1, pp. 74–77 (1968).

*Primary Examiner*—Glennon H. Hollrah
*Attorney, Agent, or Firm*—Denis A. Polyn

[57] ABSTRACT

Herbicidally active thiocarbamates are employed in combination with organophosphorothioates and -dithioates and -phosphonothioates, -dithioates and -trithioates, the latter in sufficient quantity to prevent soil degradation of the former. As a result, the herbicidal effectiveness of the thiocarbamate is significantly enhanced and prolonged, rendering a single application of the herbicide effective over a longer period of time. Such herbicidal compositions can optionally contain a non-phytotoxic antidotally effective amount of an amide of haloalkanoic or dihaloalkanoic acid.

14 Claims, No Drawings

HERBICIDE COMPOSITIONS OF EXTENDED SOIL LIFE

CROSS REFERENCE TO RELATED APPLICATIONS

This is a continuation-in-part of U.S. patent application Ser. No. 507,616, filed Jun. 24, 1983; now abandoned which in turn is a continuation-in-part of U.S. patent application Ser. No. 304,216, filed Sept. 21, 1981; now abandoned which in turn is a continuation-in-part of U.S. patent application Ser. No. 198,034, filed Oct. 17, 1980, now abandoned; which in turn is a continuation of U.S. patent application Ser. No. 060,603, filed Jul. 27, 1979, now abandoned; which in turn is a continuation-in-part of U.S. patent application Ser. No. 944,094, filed Sept. 20, 1978, now abandoned.

BACKGROUND OF THE INVENTION

This invention relates to herbicidal compositions and methods of use. In particular, this invention relates to herbicidal compositions comprising an herbicidally active thiocarbamate in combination with an organophosphorus compound, the latter serving to prolong the effectiveness of a single application of the thiocarbamate herbicide in controlling undesired plant growth.

Thiocarbamates are well known in the agricultural art as herbicides useful for weed control in crops such as corn, potatoes, beans, beets, spinach, tobacco, tomatoes, alfalfa, and others. Thiocarbamates are primarily used in pre-emergence application. They have been found to be particularly effective when incorporated into the soil prior to the planting of the crop. As a herbicide, the thiocarbamate is most concentrated immediately after its application. How long thereafter the initial concentration is retained depends in large part on the particular soil used. Thus the rate at which the thiocarbamate herbicide concentration declines following its application tends to vary from one type of soil to the next. This is evident both in the observable extent of actual weed control and in the detectable presence of undegraded thiocarbamate remaining in the soil after considerable time has elapsed.

It has now been discovered that the soil persistence of certain herbicidally active thiocarbamates is significantly extended by the incorporation of certain organophosphorus compounds, which have no herbicidal activity of their own, into the herbicide formulation. This improvement in the soil persistence of the thiocarbamate can manifest itself in a variety of ways. Improved soil persistence can be shown by herbicidal efficacy tests, wherein the degree of weed injury is measured after a set period of time following application of the herbicide. In such a test, the organophosphorus compound, which has no herbicidal activity of its own, is shown to increase the herbicidal effectiveness of the thiocarbamate by increasing the persistence of the latter in the soil, and thus prolonging its effective life. Also demonstrated herein are soil persistence test results which evidence by periodic soil analyses that the number of thiocarbamate herbicide molecules that degrade in the soil is lessened in the presence of an organophosphorus extender of this invention.

BRIEF DESCRIPTION OF THE INVENTION

This invention relates to a novel herbicidal composition comprising (a) an herbicidally effective amount of a thiocarbamate having the formula $$R^1-S-\overset{\overset{O}{\|}}{C}-N\overset{R^2}{\underset{R^3}{\diagdown}}$$

in which
$R^1$ is $C_1$-$C_6$ alkyl,
$R^2$ is $C_1$-$C_6$ alkyl,
$R^3$ is $C_1$-$C_6$ alkyl or cyclohexyl; and
(b) an amount of an organophosphorus compound having the formula $$\underset{R^5}{\overset{R^4-Y}{\diagdown}}\overset{\overset{S}{\|}}{P}-X-R^6$$

in which
$R^4$ is $C_1$-$C_6$ alkyl, $C_3$-$C_6$ alkenyl, $C_3$-$C_6$ alkynyl, or $C_5$-$C_7$ cycloalkyl, and is optionally substituted with one or members selected from halo, cyano, $C_1$-$C_3$ alkoxy, and $C_1$-$C_3$ alkylthio,
$R^5$ is $C_1$-$C_4$ alkyl, $C_1$-$C_4$ alkoxy, or $C_1$-$C_4$ alkylthio,
$R^6$ is $C_1$-$C_{10}$ alkyl, $C_2$-$C_{10}$ alkenyl, or $C_2$-$C_4$ alkynyl, optionally substituted with one or more members selected from halo, nitro, cyano, $C_1$-$C_3$ alkoxy, and $C_1$-$C_3$ alkylthio, $C_5$-$C_7$ cycloalkyl, or
-$(R^7)_m$-$\phi$ in which
$R^7$ is $C_1$-$C_4$ alkyl, $C_2$-$C_4$ alkenyl, or $C_2$-$C_4$ alkynyl, optionally substituted with one or more members selected from halo and cyano,
m is zero or one, and
$\phi$ is phenyl or phenylthio optionally substituted with one or more members selected from halo, trifluoromethyl, cyano, nitro, $C_1$-$C_3$ alkyl, $C_1$-$C_3$ alkoxy, $C_1$-$C_3$ carbalkoxy, $C_1$-$C_3$ alkylsulfinyl, formyl, $\alpha$-nitrovinyl, $\alpha$-ethylthio-$\alpha$-cyanovinyl, $\alpha$-cyanovinyl, and $\alpha$-butynyl,
X is oxygen or sulfur, and
Y is oxygen or sulfur, sufficient to extend the soil life of said thiocarbamate.

In a preferred embodiment of the invention, the compounds shown above are defined such that
$R^1$, $R^2$, $R^3$ and Y are defined as above, and
$R^4$ is $C_1$-$C_6$ alkyl other than tertiary butyl, optionally substituted with halo, or is $C_3$-$C_6$ alkenyl optionally substituted with cyano;
$R^5$ is $C_1$-$C_4$ alkyl, straight-chain $C_1$-$C_6$ alkoxy or $C1$-$C4$ alkylthio other than tertiary butylthio;
$R^6$ is $C_1$-$C_4$ alkyl substituted with one $C_1$-$C_3$ alkylthio group; $C_5$-$C_7$ cycloalkyl; $C_1$-$C_4$ alkylimino optionally usbstituted with one, two or three halogen atoms; phenyl optionally substituted with nitro, ortho-nitro and halo, $C_1$-$C_3$ alkylsulfinyl, $\alpha$-pentynyl, or trifluoromethyl; benzyl optionally substituted with halo; or is -$(R^7)$-$\phi$ in which
$R^7$ is $C_1$-$C_4$ alkylene substituted with either cyano or with one, two or three halogen atoms; and $\phi$ is phenyl substituted with halo when $R_7$ is substituted with cyano but is phenylthio substituted with halo when $R_7$ is substituted with one, two or three halogen atoms;
X is oxygen or sulfur; with the provisos that:

when $R^6$ is $C_5$-$C_7$ cycloalkyl, substituted or unsubstituted phenyl, or substituted or unsubstituted benzyl, then X must be oxygen;

when $R^4$ is allyl, Y is oxygen, and $R^6$ is para-nitrophenyl, then $R^5$ is other than methyl; and when $R^4$ methyl and $R^6$ is phenyl, then $R^5$ is other than $C_1$-$C_4$ alkylthio or ethoxy; in an amount sufficient to extend the soil life of said thiocarbamate.

In a second preferred embodiment, the compounds are defined such that $R^1$, $R^2$, $R^3$ and Y are defined as above;

$R^4$ is $C_1$-$C_6$ alkyl other than tertiary butyl, optionally substituted with halo;

$R^5$ is ethyl, straight-chain $C_1$-$C_4$ alkoxy, or $C_1$-$C_4$ alkylthio other than tertiary butylthio;

$R^6$ is $C_5$-$C_7$ cycloalkyl, benzyl or phenyl optionally substituted with either halo, ortho-nitro and halo;

X is oxygen;

with the proviso that wherein $R^4$ is methyl, Y is oxygen or sulfur, and $R^6$ is phenyl than $R^5$ is other than $C_1$-$C_4$ alkylthio or ethoxy.

In a third preferred embodiment, the compounds are defined such that $R^1$, $R^2$, $R^3$ and Y are defined as above;

$R^4$ is ethyl, n-propyl, or n-butyl;

$R^5$ is methoxy, ethoxy, n-propoxy, ethylthio, or n-propylthio;

$R^6$ is $C_5$-$C_7$ cycloalkyl, benzyl or phenyl optionally substituted with halo;

X is oxygen;

with the proviso that wherein Y is sulfur, $R^4$ is ethyl, n-propyl or n-butyl and $R^6$ is phenyl, then $R^5$ is other than methoxy.

This invention further relates to a method of controlling undesirable vegetation comprising applying the above composition to the locus where control is desired.

As used herein, the term "alkyl," "alkenyl," and "alkynyl" are intended to include both straight-chain and branched-chain radicals unless otherwise indicated. All carbon atom ranges are intended to be inclusive of their upper and lower limits.

The term "halogen atom" or "halo" is used to designate fluorine, chlorine, bromine, or iodine atoms, as well as any combination thereof.

The term "herbicide," as used herein, means a compound which adversely controls or modifies the growth of plants. By the term "herbicidally effective amount" is meant an amount of compound which causes an adverse modifying effect upon the growth of plants. By "plants" is meant germinant seeds, emerging seedlings and established vegetation, including roots and aboveground portions. Such adverse controlling or modifying effects include all deviations from natural development, for example, killing, retardation, defoliation, desiccation, regulation, stunting, tillering, stimulation, leaf burn, dwarfing and the like.

The phrase "to extend the soil life of said thiocarbamate" is used herein to denote the effect whereby herbicidal effectiveness of the thiocarbamate is maintained in substantially the same form it assumed when first applied to the locus. An extended soil life can be manifest in a slower rate of decline of weedkilling potency.

DETAILED DESCRIPTION OF THE INVENTION

According to the present invention, the above-described organophosphorus compound is added to the thiocarbamate in order to prolong the molecular integrity and herbicidal effectiveness of the latter. As the examples below indicate, there is no critical range of the ratio of these two components. The soil-life-extending effect is observable over a broad range of ratios. It is most convenient, however, to apply the compounds in a weight ratio of from about 0.1:1 to about 50:1 (thiocarbamate: organophosphorus). Preferably, the weight ratio ranges from about 1:1 to about 25:1, and most preferably from about 1:1 to about 15:1.

Examples of thiocarbamates which are useful in the present invention are S-ethyl N,N-di-n-propylthiocarbamate, S-ethyl N,N-diisobutylthiocarbamate, S-n-propyl N,N-di-n-propylthiocarbamate, S-n-propyl-N-ethyl-N-n-butylthiocarbamate, and S-ethyl-N-ethyl-N-cyclohexyl thiocarbamate.

Examples of organophosphorus compounds which are useful in the present invention are O,O-diethyl-O-phenyl phosphorothioate, O,O-diethyl-O-benzyl phosphorothioate, O-ethyl-O-phenyl-S-n-propyl phosphorodithioate, O-ethyl-S-ethyl-O-phenyl phosphorodithioate, O-ethyl-O-phenyl-S-n-butyl phosphorodithioate, O,O,-diethyl-O-cyclohexyl phosphorothioate, O,O,-diethyl-O-meta-clorophenyl phosphorothioate, O-butyl-O-methyl-O-phenyl phosphorothioate, O,O-di-n-propyl-O-phenyl phosphorothioate, O,O,-dimethyl-O-benzyl phosphorothioate, O-2-chloroethyl-O-ethyl-O-phenyl phosphorothioate, O-ethyl-O-phenyl-S-isobutyl phosphorodithioate, O-n-propyl-S-ethyl-O-phenyl phosphorodithioate, and O-phenyl-O-n-propyl-S-n-propyl phosphorodithioate. Further examples are listed in the test dat shown below.

The usefulness of many thiocarbamates as herbicides can be significantly broadened to include a wider variety of crops by the inclusion of an antidote in the herbicide formulation. The antidote protects the crop from injury by the herbicide, increasing the tolerance of the crop for the herbicide. The herbicide is thus rendered more selective in its action, retaining its potency against the undesired weeds, while showing a decreased herbicidal effect against the desired crop species. The antidotes which are especially effective in protecting crops from thiocarbamate herbicides can be described as amides of haloalkanoic acids. Such antidotes are preferably amides of dihaloalkanoic acid, such as, dichloroacetic acid. Said haloalkanoic or dihaloalkanoic acids preferably have 2 to 7 carbon atoms.

For antidote descriptions and methods of use, reference is made to U.S. Pat. No. 3,959,304, issued to Teach on May 25, 1976 ; U.S. Pat. No. 3,989,503, issued to Pallos et al. on Nov. 2, 1976; U.S. Pat. No. 4,021,224, issues to Pallos et al. on May 3, 1977; U.S. Pat. No. 3,131,509, issued to Hoffman on May 5, 1964; U.S. Pat. No. 3,564,768, issued to Hoffman on Feb. 3, 1971; U.S. Pat. No. 4,137,070, issued to Pallos et al. on Jan. 30, 1979; U.S. Pat. No. 4,294,764, issued to Rinehart on Oct. 13, 1981; U.S. Pat. No. 4,256,481, issued to Gardi et al. on May 17, 1981; U.S. Pat. No. 4,415,353, issued to Pallos et al. on Nov. 15, 1983; U.S. Pat. No. 4,415,352, issued to Pallos et al. on Nov. 15, 1983.

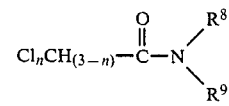

in which n is 1 or 2, and $R^8$ and $R^9$ are independently $C_1$-$C_{12}$ and alkyl, $C_2$-$C_{12}$ alkenyl, $C_1$-$C_4$ alkylene substituted with phenyl, dialkoxyalkyl wherein the alkoxy and alkyl groups each have 1-4 carbon atoms, and $C_1$-$C_4$ alkylene substituted with a 5- to 8-membered heterocyclic ring.

Preferable embodiments of said antidotes include those wherein n is 1 or 2, $R^8$ and $R^9$ are independently $C_1$-$C_6$ alkyl, $C_2$-$C_6$ alkenyl, dialkoxyethyl, cyclic acetal or $C_1$-$C_2$ alkylene substituted with phenyl. Further preferred embodiments include those antidotes wherein n is 2, $R^8$ and $R^9$ are independently $C_1$-$C_4$ alkyl, $C_2$-$C_4$ alkenyl, dimethoxyethyl, dioxolanylmethyl or benzyl. Examples falling within the above formul are N,N-diallyl dichloroacetamide, N,N-diallyl chloroacetamide, N-allyl-N2,2-dimethoxyethyl dichloroacetamide, N-allylN-[2-(1,3-dioxolanyl)]-methyl dichloroacetamide and 2,2-dichloro-N-ethyl-Nbenzyl acetamide.

Further useful antidotes are oxazolidines and thiazolidines having the formula

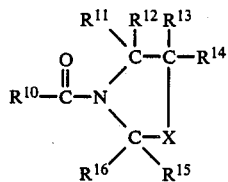

in which $R^{10}$ is $C_1$-$C_4$ alkyl, haloalkyl, or dihaloalkyl, $R^{11}$, $R^{12}$, $R^{13}$, $R^{15}$ and $R^{16}$ are each independently hydrogen or methyl, $R^{14}$ is hydrogen, methyl or phenyl, and X is oxygen or sulfur. Examples of such antidotes include 2,2,5-trimethyl-N-dichloroacetyl oxazolidine ($R^{10}$=CHCl$_2$, $R^{11}$=$R^{12}$=$R^{13}$ thiazolidine ($R^{10}$=CHCl$_2$; $R^{11}$=$R^{12}$=$R^{13}$=$R^{14}$=H; $R^{15}$=$R^{16}$=$R^{17}$=CH$_3$; X=O); 2,2-dimethy-N-dichloroacetyl thiazolidine ($R^{10}$=CHCL$_2$; $R^{11}$=$R^{12}$=$R^{13}$=$R^{14}$=H; $R^{15}$=$R^{16}$=CH$_3$; X=S); and 2,2-dimethyl-3-dichloroacetyl-5-phenyl oxazolidine ($R^{11}$=$R^{12}$=$R^{13}$=H; $R^{14}$=phenyl; $R^{15}$=$R^{16}$=CH$_3$).

Further useful antidotes are dichloroacetamide derivatives having the formula

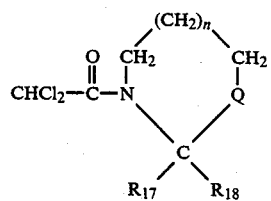

in which
Q is oxygen, sulfur, SO or SO$_2$;
n is 0 or 1, and
$R^{17}$ and $R^{18}$ are identical or different and represent hydrogen, alkyl or halophenyl, hydroxyl or nitro; or
$R^{17}$ and $R^{18}$ together form a butylene, pentylene or hexylene group which can be substituted with one or two methyl groups, with the proviso that if n=0, $R^{17}$ and $R^{18}$ are not hydrogen, alkyl or substituted phenyl.

A preferable embodiment of said antidotes include those wherein Q and n are defined as above and $R^{17}$ and $R^{18}$ together form an unsubstituted butylene, pentylene or hexylene ring, or a butylene, pentylene or hexylene ring substituted by 1 or 2 methyl groups. Examples of such antidotes include N-dichloroacetyl-1-oxa-5-azaspiro-(5,5)-undecan; N-dichloroacetyl-1-oxa-4-azaspiro-(4,5)-decane; N-dichloroacetyl-10-methyl-1-oxa-4-azaspiro-(4,5)-decane; N-dichloroacetyl-8-methyl-1-oxa-4-azaspiro-(4,5)-decane; N-dichloroacetyl-6,10-dimethyl-1-oxa-4-azaspiro-(4,5)-decane; N-dichloroacetyl-1-thia-4-azaspiro-(4,5)-decane; N-dichloroacetyl-1-oxa-5-azaspiro-(5,6)-dodecane; and N-dichloroacetyl-1-oxa-4-azaspiro-(4,4)-nonane.

A still further useful antidote is 1,8-naphthalic anhydride.

The antidote is applied in conjunction with the thiocarbamate and the organophosphorus compound in a nonphytotoxic antidotally effective amount. By "nonphytotoxic" is meant an amount of the antidote which causes at most minor injury to the desired crop species. By "antidotally effective" is meant an amount of the antidote which substantially decreases the extent of injury caused by the thiocarbamate to the desired crop species. The preferred weight ratio of herbicide to antidote is from about 0.1:1 to about 30:1. The most preferred weight ratio range is from about 3:1 to about 20:1.

The following examples are offered to illustrate the compositions, methods, and effectiveness of the present invention, and are not intended to limit the invention in any way.

EXAMPLE 1

Herbicidal Activity Improvement Tests

This example offers herbicidal activity test data for many representative extender compounds within the scope of this invention showing their effectiveness in improving the herbicidal activity of thiocarbamates. The effect is observed by comparing the extent of weed control in test flats treated with a thiocarbamate against that occuring in similar flats treated with both the thiocarbamate and the extender. The soil used in these tests was a sandy loam soil from Sunol, Calif., which was pre-treated with the herbicide to simulate a typical field which had received previous herbicide applcations. The Sunol sandy loam soil analyzed as follows: sand 63.1%; silt-21.2%; clay-12.4%, organic matter-1%; and pH 6.9

A. Soil Pre-Treatment

A solution was prepared by diluting an emulsifiable liquid concentrate containing 6 lb/gal (0.72 kg/l) (76.8% by weight) of the herbicide S-ethyl di-n-propylthiocarbamate in 200 ml of water, such that the resulting concentration of herbicide in the solution was 2000 mg/l. Two hundred ml of this solution was then added to 200 lb (90.8 kg) of soil to which 17-17-17 fertilizer had been previously added to a concentration of 50 ppm by weight with respect to the soil. The mixture was mixed in a rotary mixer for 10 to 30 minutes.

The soil was then placed in round plastic containers, 7.5 inches (19.0 cm) in diameter by 7.5 inches (19.0 cm) deep. The soil was tamped and leveled with a row marker to impress one row across the width of each container. This row was seeded with watergrass (*Echinochloa crus-galli*). Sufficient seeds were planted to produce several seedlings. The containers were then placed in a greenhouse maintained at 20° C. to 30° C. and watered daily by sprinkler.

Five weeks after treatment, the soil was allowed to dry out and the plant foliage was removed. The soil was then passed through a 0.25 inch (0.64 cm) screen to remove plant roots and clods.

B. Herbicide Test

A solution was prepared by diluting an emulsifiable liquid concentrate containing 6 lb/gal. (0.72 kg/l) (76.8% by weight) of the herbicide S-ethyl N,N-di-n-propylthiocarbamate in 675 ml of water such that the resulting concentration of herbicide in the solution was 1.48 mg/ml. Five ml of this solution when added to three pounds of soil yielded a quantity in the soil equivalent to three pounds per acre.

The extender compounds were used in technical form. These materials were added 5 ml acetone and 14.5 ml water such that the resulting concentration of the extender in the solution was 1.54 mg/ml. Five ml of this solution when added to three pounds of soil yielded a quantity in the soil equivalent to four pounds per acre.

Five ml of the extender solution and 5 ml of the herbicide solution were tank-mixed. The resultant mixture of 10 ml was then added to 3 lbs of soil and incorporated into the soil by a rotary mixer. Thus, 10 ml of the mixture and 3 pounds of soil were placed in rotary mixer and incorporated.

The treated soil was then placed in aluminum flats which were approximately 3 inches deep, 4 inches wide, and 8 inches long (7.6×10.2×20.3 cm). The soil was tamped and leveled with a row marker to impress six rows across the width of the flat. The test weeds were as follows:

| COMMON NAME | ABBREVIATION | SCIENTIFIC NAME |
|---|---|---|
| watergrass | WG | *Echinochloa crus-galli* (L.) |
| wild oats | WO | *Avena fatua* (L.) |
| wild cane | WC | *Sorghum bicolor* (L.) Moench |

R-10 milo (*Sorghum bicolor*) was also used as a plant growth indicator. Two rows of watergrass were planted.

One row of DeKalb XL-25A corn of species *Zea mays* (L.) was planted.

Sufficient seeds were planted to produce several seedlings per inch in each row. The flats were then placed in a greenhouse maintained at 70° to 85° F. (21° to 30° C.) and watered daily by sprinkler.

Approximately three weeks after treatment, the degree of weed control and corn injury were estimated and recorded as a percentage compared to the growth of the same species in a check flat of the same age which had been seeded in conditioned soil but not treated with either an herbicide or an extender. The rating scale ranges from 0 to 100%, where 0 equals no effect with plant growth equal to the untreated check, and 100 equals complete kill.

The results are listed in Table 1. The average percentage of weed control in the last column is the average for the above-identified weed species and plant growth indicator. There was no injury to the corn in any of the tests. Control experiments (herbicide alone with no extender present) were included in each batch for comparison. Substantial improvements in average percent weed control over the control experiments are evident. The herbicidal efficay of the thiocarbamate three weeks after application was much improved by the use of the extender, whereas the corn remained unaffected.

An asterisk (*) indicates the percentage is an average of two trials.

TABLE 1

Herbicidal Activity
Herbicide: S-ethyl N,N-di-n-propyl thiocarbamate
Application Rate: Herbicide 3 lb/A - Extender 4 lb/A
Herbicide Alone: 10% Average Weed Control
Rating Time: Two weeks after treatment.

| Cmpd. No. | $R^4$—Y— | $R^3$— | —X—$R^6$ | Ave. % Weed Control |
|---|---|---|---|---|
| 1 | $C_2H_5O$— | $C_2H_5O$— | 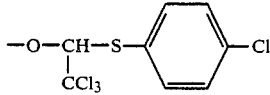 | 38% |
| 2 | $C_2H_5O$— | $C_2H_5$— | 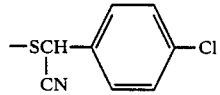 | 40% |
| 3 | $CH_3CH=CHCH_2O$— | $C_2H_5$— | 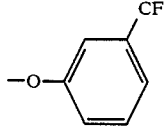 | 38% |
| 4 | $C_2H_5O$— | $C_2H_5O$— | 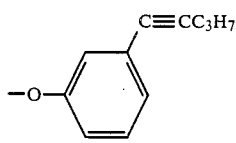 | 34% |

TABLE 1-continued

Herbicidal Activity
Herbicide: S-ethyl N,N-di-n-propyl thiocarbamate
Application Rate: Herbicide 3 lb/A - Extender 4 lb/A
Herbicide Alone: 10% Average Weed Control
Rating Time: Two weeks after treatment.

| Cmpd. No. | $R^4$—Y— | $R^3$— | —X—$R^6$ | Ave. % Weed Control |
|---|---|---|---|---|
| 5 | $(CH_3)_2CHCH_2CH_2O$— | $C_2H_5$— | 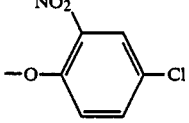 | 47% |
| 6 | $C_2H_5O$— | $C_2H_5O$— | $-O-N=CHC(Cl)-CHCH_3$ with Cl, Cl substituents 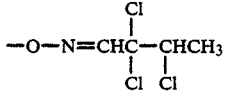 | 34% |
| 7 | $CH_2=CHCH_2O$— | $C_2H_5$— | 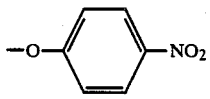 | 34% |
| 8 | $n\text{-}C_4H_9S$— | $C_2H_5$— | $-SCH_2SCH_2CH_3$ | 35% |
| 9 | $CH_3O$— | $CH_3O$— | 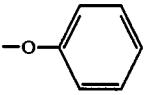 | 37% |
| 10 | $C_2H_5O$— | $C_2H_5O$— | 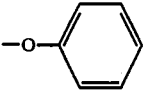 | 85%* |
| 11 | $CH_3O$— | $CH_3O$— | 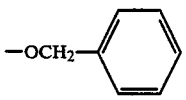 | 55% |
| 12 | $C_3H_7O$— | $C_3H_7O$— | 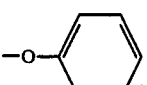 | 69% |
| 13 | $C_2H_5O$— | $C_2H_5O$— | 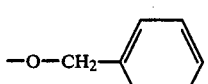 | 96% |
| 14 | $C_2H_5O$— | $C_2H_5O$— | 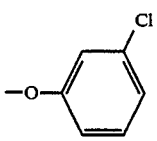 | 70% |
| 15 | $C_2H_5O$— | $C_2H_5O$— | 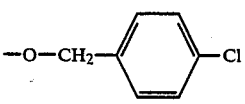 | 42% |
| 16 | $C_2H_5O$— | $C_2H_5O$— | 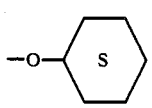 | 76% |

TABLE 1-continued

Herbicidal Activity
Herbicide: S-ethyl N,N-di-n-propyl thiocarbamate
Application Rate: Herbicide 3 lb/A - Extender 4 lb/A
Herbicide Alone: 10% Average Weed Control
Rating Time: Two weeks after treatment.

| Cmpd. No. | R⁴—Y— | R³— | —X—R⁶ | Ave. % Weed Control |
|---|---|---|---|---|
| 17 | C₂H₅O— | CH₃O— | —O—C₆H₅ | 39% |
| 18 | n-C₄H₉O— | CH₃O— | —O—C₆H₅ | 65% |
| 19 | ClC₂H₄O— | C₂H₅O— | —O—C₆H₅ | 55% |
| 20 | C₂H₅O— | C₂H₅S— | —O—C₆H₅ | 92% |
| 21 | C₂H₅O— | n-C₃H₇S— | —O—C₆H₅ | 96% |
| 22 | C₂H₅O— | i-C₃H₇S— | —O—C₆H₅ | 45% |
| 23 | CH₃(CH₂)₃S— | C₂H₅O— | —O—C₆H₅ | 90% |
| 24 | sec-C₄H₉S— | C₂H₅O— | —O—C₆H₅ | 34% |
| 25 | i-C₄H₉S— | C₂H₅O— | —O—C₆H₅ | 57% |
| 26 | n-C₃H₇O— | C₂H₅S— | —O—C₆H₅ | 68% |
| 27 | n-C₃H₇O— | n-C₃H₇S— | —O—C₆H₅ | 64% |
| 28 | i-C₃H₇S— | n-C₃H₇O— | —O—C₆H₅ | 37% |

The last two provisos in the first preferred embodiment, supra, were designed to delete organophosphorus compounds which were tested according to the procedures of this example but did not show significant extending activity.

The compounds referred to by said provisos are those listed below in Table A.

TABLE A

| | $R^4$—Y— | $R^5$— | —X—$R^6$ |
|---|---|---|---|
| Proviso 2 | $CH_2$=$CHCH_2O$— | $CH_3$— | —O—⟨⟩—$NO_2$ |
| Proviso 3 | $CH_3S$— | $CH_3S$— | —O—⟨⟩ |
| | $CH_3S$— | $C_2H_5O$— | —O—⟨⟩ |
| | $CH_3O$— | $C_2H_5S$— | —O—⟨⟩ |
| | $CH_3O$— | n-$C_3H_7S$— | —O—⟨⟩ |
| | $CH_3O$— | i-$C_3H_7S$— | —O—⟨⟩ |
| | $CH_3O$— | n-$C_4H_9S$— | —O—⟨⟩ |

The following Examples 2-13 demonstrate the effectiveness of the organophosphorus extenders of this invention in slowing the rate of degradation of thiocarbamates herbicides (Examples 2,4) and of extending the soil life of thiocarbamates by bioassay results as in Example 1, above (Examples 3, 5, 6, 7, 8, 9, 10, 11, 12, and 13).

Example 3 shows the activity of a variety of organophosphorus compounds with S-ethyl N,N-di-n-propyl thiocarbamate with and without an antidote in a number of different types of soils that has a prior history of thiocarbamate herbicide treatment.

Example 4 presents chemical analyses indicating as does Example 2 the slowed degradation of thiocarbamate herbicides in the presence of an organophosphorus compound of this invention. In Example 4, however, the soil was pre-treated with a thiocarbamate herbicide in the greenhouse.

Examples 5-7, 9 and 11-13 show bioassay results indicating the effectiveness of representative extenders in extending the soil life of a variety of thiocarbamate herbicides in compositions with and without a variety of antidotes.

Example 8 shows a thiocarbamate herbicide, an antidote and an extender tested alone and in combination in soil which had not been pretreated with a thiocarbamate herbicide.

Example 10 was designed to show that a representative extender when tested alone in soil pre-treated with a thiocarbamate herbicide has no herbicidal activity.

EXAMPLE 2

Soil Persistence Tests

This example shows, by periodic chemical analyses of soil composition, the effectiveness of the organophosphorus compounds of the present invention in slowing down the rate of degradation of the thiocarbamate herbicide.

A one-pint (0.5 liter) glass canning jar containing 250 grams (g) of soil (on an air-dry basis) was used for each test. Soils of three different textures were used: a loamy sand from Sunol, Calif.; a silty loam from Thurman, Iowa; and a loam from Tracy, Calif. All of these soils had a prior history of thiocarbamate herbicide treatment. The relative amounts of sand, silt, and clay of each soil type were determined by mechanical means, and the quantity of organic matter and the acidity (pH) were determined chemically. The results of these analyses are shown below:

| | Soil Analyses | | | | |
|---|---|---|---|---|---|
| | Composition (Weight %) | | | Organic Matter | |
| Source | Sand | Silt | Clay | (Weight %) | pH |
| Sunol, CA | 64 | 29 | 7 | 4 | 6.8 |
| Thurman, IA | 32 | 56 | 12 | 3 | 7.2 |
| Tracy, CA | 50 | 30 | 20 | 4.7 | 6.1 |

The test compounds or combinations were dissolved in water at concentrations calculated such that a 5.0 cubic centimeter (cc) aliquot contained quantities of active ingrediens equivalent to the desired application rates when added to the jar. The thiocarbamates used in these tests were applied in the form of emulsifiable liquid concentrates containing an antidote to prevent crop injury. The concentrates were appropriately diluted to correspond to an application rate of 6.0 lb/A (6.72 kilograms/hectare) of active ingredient. Of the organophosphorus compounds tested, O,O-diethyl-O-phenyl phosphorothioate was applied as a technical liquid diluted for an application rate of 0.5 lb/A (0.56 kilograms/hectare) or 1.0 lb/A (1.12 kilograms/hectare), and O-ethyl-S-phenyl ethylphosphonodithioate was applied as an emulsifiable liquid concentrate diluted for an application rate of 4.0 lb/A (4.48 kilograms/hectare) of active ingredient.

Thus, a 5.0 cc aliquot of an aqueous mixture, containing the thiocarbamate, the antidote, and the organophosphorus additive in appropriate concentrations, was transferred by pipette to the jar and incorporated into the soil with a spatula. The jar was then sealed with a lid and shaken manually for approximately thirty seconds.

Following such treatment, the soil was seeded with approximately fifty barnyardgrass (Echinochloa crusgalli) seeds and two seeds of DeKalb XL-45A corn. The soil was then moistened to field capacity and the jar was placed unsealed in a greenhouse where the temperature was maintained at approximately 70° to 80° F. (21° to 27° C.) and the soil was moistened periodically.

The tests were performed in duplicate and a separate jar was used for each test. After a specified interval, two jars were removed from the greenhouse, stripped of their foliar plant material, sealed tightly, and frozen to await chemical analysis. After an additional interval, a second pair was removed and similarly treated. In all, six such pairs for each application rate were prepared for analysis, including one pair taken immediately after treatment with the test chemicals for use as a zero time treatment.

Each prepared sample was macerated with 2.0 liters of water in a Waring Blender, then transferred to a 4.0 liter flask. Approximately 10.0 milliliters (ml) of an anti-foaming agent was added. The mixture was distilled rapidly, and approximately 400 ml of distillate was collected. Five drops of concentrated hydrochloric acid were added to the distillate to suppress emulsion formation. The thiocarbamate was extracted from the distillate with two 4.0 ml portions of isooctane. The extracts were then combined for analysis for thiocarbamate content by gas chromatography.

In Tables 2 and 3, the chromatogram data has been converted to equivalent soil concentrations in parts per million (ppm) by weight of thiocarbamate. These tables list the results as averages for each pair of duplicates.

The tables clearly show that the thiocarbamate content declined with time in each type of soil tested. They further show that such decline was substantially lessened by the presence of the organophosphorus compound. The effect of the organophosphorus compound on the Sunol soil is particularly evident from 21 days on in Table 2 and from three weeks on in Table 3, by comparing the experimental entries with control. The higher figures for the experimental entries are a clear indication that the rate of decline is substantially decreased due to the presence of the organophosphorus compound. A similar effect on the Tracy soil is evident from three days on in Table 2 and from one week on in Table 3. Finally, a similar effect is observed in the Thurman soil from seven days on in Table 2 and from two weeks on in Table 3.

TABLE 2

Soil Persistence Test Results

Herbicide: S-ethyl N,N-di-n-propylthiocarbamate (active ingredient) in 12:1 weight ratio with N,N-diallyl dichloroacetamide (antidote)
Herbicide Application Rate: 6.0 lb/A

| Organophosphorus Additive | Additive Application Rate (lb/A) | Amount of Herbicide Present in Soil (ppm active ingredient)[a] Days Following Application | | | | | |
|---|---|---|---|---|---|---|---|
| | | 0 | 3 | 7 | 14 | 21 | 28 |
| Soil used: from Sunol, California | | | | | | | |
| None (control) | — | 11.71 | 9.97 | 7.88 | 6.12 | 0.76 | 0.71 |
| O,O-diethyl-O-phenyl phosphorothioate | 0.5 | 11.43 | 10.25 | 8.41 | 6.88 | 5.38 | 2.28 |
| O,O-diethyl-O-phenyl phosphorothioate | 1.0 | 12.10 | 10.23 | 10.91 | 6.79 | 5.74 | 3.95 |
| O-ethyl-S-phenyl ethylphosphonodithioate | 4.0 | 10.36 | 11.70 | 8.05 | 5.17 | 3.18 | 1.04 |
| Soil used: from Tracy, California | | | | | | | |
| None (control) | — | 10.59 | 2.58 | 0.24 | 0.12 | 0.00 | —[b] |
| O,O-diethyl-O-phenyl phosphorothioate | 0.5 | 12.05 | 9.05 | 7.26 | 0.82 | 0.41 | — |
| O,O-diethyl-O-phenyl phosphorothioate | 1.0 | 12.02 | 10.04 | 7.58 | 1.23 | 0.38 | — |
| O-ethyl-S-phenyl ethylphosphonodithioate | 4.0 | 10.24 | 9.54 | 1.48 | 0.30 | 0.00 | — |
| Soil used: from Thurman, Iowa | | | | | | | |
| None (control) | — | 15.79 | 8.75 | 0.40 | 0.27 | 0.22 | — |
| O,O-diethyl-O-phenyl phosphorothioate | 0.5 | 12.24 | 9.38 | 5.87 | 0.51 | 0.43 | — |
| O,O-diethyl-O-phenyl phosphorothioate | 1.0 | 12.68 | 10.88 | 9.26 | 0.55 | 0.39 | — |
| O-ethyl-S-phenyl ethylphosphonodithioate | 4.0 | 11.47 | 8.88 | 4.29 | 0.24 | 0.18 | — |

[a]Each figure shown represents the average of two samples.
[b]Dashes represent samples not analyzed.

TABLE 3

Soil Persistence Test Results

Herbicide: S-ethyl N,N-diisobutylthiocarbamate (active ingredient) in 24:1 weight ratio with N,N-diallyl dichloroacetamide (antidote)
Herbicide Application Rate: 6.0 lb/A

| Organophosphorus Additive | Additive Application Rate (lb/A) | Amount of Herbicide Present in Soil (ppm active ingredient)[a] Weeks Following Application | | | | | |
|---|---|---|---|---|---|---|---|
| | | 0 | 1 | 2 | 3 | 4 | 5 |
| Soil used: from Sunol, California | | | | | | | |
| None (control) | — | 9.00 | 7.30 | 6.15 | 3.35 | 0.68 | 0.30 |
| O,O-diethyl-O-phenyl phosphorothioate | 1.0 | 9.40 | 7.10 | 6.55 | 5.25 | 5.18 | 3.65 |
| Soil used: from Tracy, California | | | | | | | |
| None (control) | — | 8.05 | 1.25 | 0.13 | 0.17 | 0.07 | 0.03 |
| O,O-diethyl-O-phenyl phosphorothioate | 1.0 | 7.95 | 7.45 | 6.05 | 5.65 | 4.84 | 0.66 |
| Soil used: from Thurman, Iowa | | | | | | | |
| None (control) | — | 8.35 | 7.00 | 0.16 | 0.11 | 0.07 | 0.07 |
| O,O-diethyl-O-phenyl phosphorothioate | 1.0 | 8.35 | 7.10 | 4.90 | 2.11 | 1.18 | 0.37 |

[a]Each figure shown represents the average of two samples.

EXAMPLE 3

Herbicidal Activity Improvement Tests

This example offers herbicidal activity test data to show the effectiveness of the organophosphorus additives in improving the herbicidal activity of thiocarbamates. The effect is observed by comparing the extent of weed control in test flats treated with a thiocarbamate against that occuring in similar flats treated with both the thiocarbamate and an organophosphorus compound.

As in Example 2, the thiocarbamate used in this test was applied in the form of an emulsifiable liquid concentrate containing 6 lb/gal (0.72 kg/l) active ingredient. In several of the tests as indicated, an antidote was included in the formulation to prevent crop injury. The organophosphorus compounds were primarily used in technical form, although emulsifiable liquids, granules, and microcapsules were also used, as indicated.

Stock solutions were prepared by adding appropriate amounts of the formulated test chemicals to 100 cc mixtures containing equal parts of water and acetone. Five cc of a stock solution was then added to three pounds of soil containing approximately 5% mositure in a 5-gallon (18.9 liter) rotary mixer where the soil and stock solution were mixed for 10 to 20 seconds. Such a method of application of the herbicidal compositions is called pre-plant soil incorporation (PPI).

The soil was then placed in aluminum flats which were 2.5 inches (6.4 cm) deep, 3.5 inches (8.9 cm) wide, and 7.5 inches (19.0 cm) long. The soil was tamped and leveled with a row marker to impress six rows across the width of the flat. The seeds of six grass species were planted in the marked rows and covered with soil. The test grass species varied from test to test and including the following:

| COMMON NAME | SCIENTIFIC NAME |
| --- | --- |
| yellow foxtail | *Setaria lutescens* (Weigel) Hubb. |
| barnyardgrass | *Echinochloa crus-galli* (L.) Beauv. |
| milo | *Sorghum bicolor* (L.) Moench |
| barley | *Hordeum vulgare* (L.) |
| giant foxtail | *Setaria faberi* Herrm |
| wild cane | *Sorghum bicolor* (L.) Moench (variant of milo) |

Corn was also planted in some of the tests. The corn used was DeKalb XL-45A corn of species Zea mays (L).

Sufficient seeds were planted to produce several seedlings per inch in each row. The flats were then placed in a greenhouse maintained at 70° to 85° F. and watered daily by sprinkler.

Three weeks after treatment, the degree of weed control and corn injury were estimated and recorded as percentage control compared to the growth of the same species in an untreated check flat of the same age. The rating scale ranges from 0 to 100%, where 0 equals no effect with plant growth equal to the untreated control, and 100 equals complete kill.

Tables 4, 5, 6 and 7 which follow list the results of these tests. A control experiment is included in each table for comparison. Substantial improvements in average percent weed control over the control experiment are evident in each table at all application rates of the organophosphorus additive. While all the data in any single table was obtained at the same time under the same conditions, variations exist from one table to the next due to the difficulty in duplicating environmental conditions on different dates. The variations are also due to the fact that different weed combinations and/or soils were used. On the whole, however, it is clear that herbicidal efficacy of the thiocarbamate three weeks after application was much improved by the use of the organophosphorus additive.

TABLE 4

Herbicidal Activity on Barley, Barnyardgrass, Milo and Giant Foxtail

| Herbicide: | S-ethyl N,N-di-n-propylthiocarbamate as 6 lb/gallon emulsifiable liquid containing, where shown, N,N-diallyl dichloroacetamide antidote in 12:1 weight ratio |
| --- | --- |
| Application Rate: | 3.0 lb/A |
| Soil Source: | Tracy, California |
| Evaluation Time: | 3 weeks after treatment |

| | | Without Antidote | | With Antidote | |
| --- | --- | --- | --- | --- | --- |
| Organophosphorus Additive | Application Rate (lb/A) | Average % Weed Control | % Corn Injury | Average % Weed Control | % Corn Injury |
| None (control). | — | 65 | 0 | 58 | 0 |
| O-ethyl-S-phenyl ethyl- | 0.5 | 92 | 60 | 95 | 0 |
| ethylphosphonodithioate | 1.0 | 100 | 100 | 100 | 20 |
| (4 E)[a] | 2.0 | 100 | 80 | 100 | 0 |
| | 4.0 | 100 | 100 | 99 | 0 |
| O-ethyl-S-phenyl ethyl- | 0.5 | 97 | 90 | 78 | 0 |
| phosphonodithioate (10 G)[b] | 1.0 | 100 | 80 | 81 | 0 |
| | 2.0 | 100 | 90 | 88 | 0 |
| | 4.0 | 100 | 90 | 99 | 10 |
| O,O-diethyl-S-ethyl- | 1.0 | 80 | 20 | | |
| thioethylphosphorodi- | 2.0 | 85 | 40 | | |
| thiaote (technical) | 4.0 | 87 | 50 | | |
| O,O-diethyl-O-p-methyl- | 1.0 | 96 | 60 | | |
| sulfinylphenylphosphoro- | 2.0 | 100 | 95 | | |
| dithioate (technical) | 4.0 | 100 | 90 | | |
| O,O-dimethyl-O-p- | 1.0 | 98 | 70 | | |
| nitropheylphosphoro- | 2.0 | 95 | 70 | | |
| thioate (technical) (technical) | 4.0 | 100 | 90 | | |

[a]4 E: Emulsifiable liquid containing 4 lb/gal active ingredient.
[b]10 G: Granular formulation containing 10% by weight active ingredient.

TABLE 5

Herbicidal Activity on Yellow Foxtail, Barnyardgrass and Wild Cane

Herbicide: S—ethyl N,N-di-n-propylthiocarbamate as 6 lb/gal emulsifiable liquid
Application Rate: 3.0 lb/A
Evalution Time: 3 weeks after treatment

| Organophosphorus Additive | Application Rate (lb/A) | Tracy, CA Soil | | Thurman, IA Soil | |
|---|---|---|---|---|---|
| | | Average % Weed Control | % Corn Injury | Average % Weed Control | % Corn Injury |
| None (control) | — | 4 | 0 | 14 | 0 |
| O,O-dimethyl-O-phenylphos- | 0.5 | 18 | 0 | 16 | 0 |
| phorothioate (technical) | 1.0 | 26 | 0 | 34 | 0 |
| | 2.0 | 30 | 0 | 44 | 0 |
| O,O-diethyl-O-phenyl- | 0.5 | 48 | 0 | 38 | 0 |
| phosphorothioate | 1.0 | 81 | 0 | 76 | 0 |
| (technical) | | | | | |
| O,O-diisopropyl-O-phenyl- | 0.5 | 40 | 0 | 30 | 0 |
| phosphorothioate | 1.0 | 42 | 0 | 46 | 0 |
| (technical) | 2.0 | 56 | 0 | 58 | 0 |
| O,O-di-n-propyl-O-phenyl- | 0.5 | 30 | 0 | 44 | 0 |
| phosphorothioate | 1.0 | 50 | 0 | 50 | 0 |
| (technical) | 2.0 | 86 | 0 | 81 | 0 |
| O,O-dimethyl-O-benzyl- | 1.0 | 32 | 0 | 32 | 0 |
| phosphorothioate | 2.0 | 54 | 0 | 38 | 0 |
| (technical) | | | | | |
| O,O-diethyl-O-(2-phenyl- | 1.0 | 32 | 0 | 32 | 0 |
| ethyl)phosphorothioate | 2.0 | 46 | 0 | 32 | 0 |
| (technical) | | | | | |

TABLE 6

Herbicidal Activity on Yellow Foxtail, Barnyardgrass, Milo and Wild Cane

Herbicide: S-ethyl N,N-di-n-propylthiocarbamate as 6 lb/gal emulsifiable liquid
Application Rate: 3.0 lb/A
Evaluation Time: 3 weeks after treatment
Soil Source: Tracy, CA

| Organophosphorus Additive | Average % Weed Control Application Rates (lb/A) at: | | | | | |
|---|---|---|---|---|---|---|
| | 0 | 0.125 | 0.25 | 0.50 | 1.0 | 2.0 |
| (control) | | | | | | |
| O-ethyl-S-phenyl ethyl- phosphonodithioate (technical) | 20 | — | 49 | 72 | 90 | 93 |
| O,O-diethyl-O-phenyl- phosphorothioate (technical) | 20 | 88 | 91 | 94 | 96 | — |
| O,O-diethyl-O-phenyl phosphorothioate (microcapsule) | 20 | 89 | 93 | 94 | 95 | — |
| O,O-dimethyl-O-phenyl- phosphorothioate (technical) | 20 | 32 | 54 | 72 | 87 | — |

TABLE 7

Herbicidal Activity on Yellow Foxtail, Barnyardgrass, Milo and Wild Cane

Herbicide: S-ethyl N,N-di-propylthiocarbamate as 6 lb/gal emulsifiable liquid
Application Rate: 3.0 lb/A
Evaluation Time: 3 weeks after treatment
Soil Source: Thurman, Iowa

| Organophosphorus Additive | Average % Weed Control Application Rates (lb/A) at: | | | | |
|---|---|---|---|---|---|
| | 0 | 0.50 | 1.0 | 2.0 | 4.0 |
| (control) | | | | | |
| O,O-diethyl-O-phenyl phos- phorothioate (technical) | 22 | 60 | 62 | 82 | 92 |
| O-ethyl-S-phenyl ethylphos- phonodithioate (technical) | 42 | 8 | 16 | 24 | 28 |
| O,O-diethyl-O-(2-phenylethyl) phosphorothioate (technical) | 22 | 14 | 20 | 46 | 64 |
| O—O-di-n-propyl-O-phenyl phosphorothioate (technical) | 22 | 38 | 50 | 70 | 84 |
| O-ethyl-S-ethyl-O-phenyl phosphorothioate (technical) | 22 | 36 | 56 | 76 | 90 |

EXAMPLE 4

Accelerated Soil Persistence Tests

The tests shown in this example are similar to those of Example 2, except that the soil was pre-treated in the greenhouse to magnify and accelerate its effect in causing the herbicide content to decline. The soil from Sunol, Calif., described in Example 2 was used in all tests.

A. Soil Pre-Treatment

A solution was prepared by diluting an emulsifiable liquid concentrate containing 6 lb/gal (0.72 kg/l) of the herbicide S-ethyl N,N-di-n-propylthiocarbamate in 100 ml of water, such that the resulting concentration of herbicide in the solution was 4000 mg/l. Five ml of this solution was then added to 10 lb (4.54 kg) of soil and the mixture was mixed in a rotary mixer for 10-20 seconds.

The soil was then placed in round plastic containers, 9 inches (22.9 cm) in a diameter by 9 inches (22.9 cm) deep. The soil was tamped and leveled with a row marker to impress three rows across the width of each container. Two rows were seeded with DeKalb XL-45A corn (*Zea mays*), and one row was seeded with barnyardgrass (*Echinochloa crus-galli*). Sufficient seeds were planted to produce several seedlings per row. The containers were then placed in a greenhouse maintained at 20° C. to 30° C. and watered daily by sprinkler.

Five weeks after treatment, the soil was allowed to dry out and the plant foliage was removed. The soil was then passed through a 0.25 inch (0.64 cm) screen to remove plant roots and clods, and then passed through a 2 millimeter (mm) screen.

B. Soil Persistence Test

A 100-gram quantity (air-dry basis) of the pre-treated soil was placed in an 8 ounce (0.24 liter) wide-mouth glass bottle. The same emulsifiable concentrate described in Part A above was appropriately diluted in water such that a 5 ml portion added to the soil would produce a herbicide concentration of 6 ppm (weight) in the soil. A selected extender compound in technical (nonformulated) form was then diluted in an acetone-water mixture such that a one ml portion added to the soil would produce a concentration of 4 ppm (weight). On these bases, the herbicide and extender were added to the bottle containing the soil. The bottle was then sealed with a lid and shaken manually for approximately 15 minutes. The bottle of soil was placed in an environmental growth chamber where the temperature was maintained at approximately 25° C.

Two days later, the bottle was removed from the environmental chamber and 50 ml of water and 100 ml of toluene were added. The bottle was then tightly sealed with a lid containing a cellophane liner, and vigorously shaken on a variable speed, reciprocating shaker (Eberback Corp. Model No. 6000) set approximately 200 excursions per minute for one hour. After shaking, the bottle contents were allowed to settle, and a 10 ml aliquot of toluene was transferred by pipette into a glass vial and sealed with a polyseal cap. The toluene extract was analyzed for herbicide content by gas chromatography. The chromatogram data was then converted to equivalent soil concentrations in parts per million (ppm) by weight of the herbicide.

The results are shown in Tables 8, 9 and 10, which represent three separate pre-treatment batches. Two control runs are included in each table (where the herbicide was applied alone). In each case, substantially more herbicide remains in the soil when an extender compound is present.

TABLE 8

2-Day Soil Persistence Tests - Run #1

| | |
|---|---|
| Herbicide: | S-ethyl N,N-di-n-propylthiocarbamate |
| Application Rate: | Herbicide 6 ppm (weight) |
| | Extender 4 ppm (weight) |
| Herbicide Alone: | Trial A: 0.22    Residue After 2 Days (ppm) |
| | Trial B: 0.23 |

Herbicide with Extender:

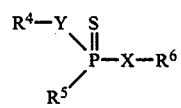

| Cmpd. No. | Extender | | | Herbicide Residue After 2 Days (ppm) |
|---|---|---|---|---|
| | $R^4$—Y— | $R^5$— | —X—$R^6$ | |
| 1 | $C_2H_5O$— | $C_2H_5O$— | 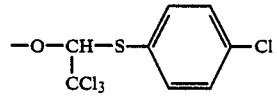 | 3.97 |

TABLE 9

2-Day Soil Persistence Tests - Run #2

| | |
|---|---|
| Herbicide: | S-ethyl N,N-di-n-propylthiocarbamate |
| Application Rate: | Herbicide 6 ppm (weight) |
| | Extender 4 ppm (weight) |
| Herbicide Alone: | Trial A: 1.42    Residue After 2 Days (ppm) |
| | Trial B: 1.23 |

Herbicide with Extender:

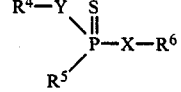

| Cmpd. No. | Extender | | | Herbicide Residue After 2 Days (ppm) |
|---|---|---|---|---|
| | $R^4$—Y— | $R^5$— | —X—$R^6$ | |
| 2 | $C_2H_5O$— | $C_2H_5$— | 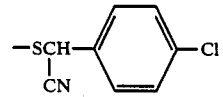 | 2.26 |

TABLE 9-continued

| | | | | |
|---|---|---|---|---|
| 3 | CH₃CH=CHCH₂O— | C₂H₅— | —O—C₆H₄—CF₃ | 2.88 |

TABLE 10

2-Day Soil Persistence Tests - Run #3

| | |
|---|---|
| Herbicide: | S-ethyl N,N-di-n-propylthiocarbamate |
| Application Rate: | Herbicide 6 ppm (weight) |
| | Extender 4 ppm (weight) |
| Herbicide Alone: | Trial A: 0.13    Residue After 2 Days (ppm) |
| | Trial B: 0.11 |

Herbicide with Extender:

$$\begin{array}{c} R^4-Y \\ \phantom{R^4-Y}\diagdown \phantom{S} \\ \phantom{R^4-Y}\phantom{\diagdown}P\overset{\displaystyle S}{=}X-R^6 \\ \phantom{R^4-Y}\diagup \\ R^5 \end{array}$$

| Cmpd. No. | Extender R⁴—Y— | R⁵— | —X—R⁶ | Herbicide Residue After 2 Days (ppm) |
|---|---|---|---|---|
| 4 | C₂H₅O— | C₂H₅O— | —O—C₆H₄—C≡CC₃H₇ | 1.08 |
| 5 | (CH₃)₂CHCH₂CH₂O— | C₂H₅— | —O—C₆H₃(NO₂)—Cl | 0.92 |

EXAMPLE 5

Herbicidal Activity Improvement Tests

The tests described in this example are similar to those of Example 3, except that 2,2,5-trimethyl-N-dichloromethyl oxazolidine was used as the antidote rather than N,N-diallyl dichloroacetamide, and the soil was pre-treated in a manner similar to that described in Example 4 to simulate a field with a history of prior treatment with the same herbicide. The herbicide was S-ethyl di-n-propylthiocarbamate, the extender compound was O,O-diethyl-O-phenyl phosphorothioate, and the soil was a sandy loam soil from San Jose, Calif.

A. Soil Pre-Treatment

The procedure of Example 4, section A, was used, with a treating solution containing 2000 mg/l of herbicide rather than 4000.

B. Herbicide Test

The pre-plant soil incorporation procedure of Example 3 was followed, using aluminum planting flats measuring 4 inches (10.2 cm) deep, 6 inches (15.2 cm) wide, and 9 inches (22.9 cm) long, and the following weed species:

| COMMON NAME | SCIENTIFIC NAME |
|---|---|
| watergrass | Echinochloa crus-galli (L.) Beauv. |
| wild oats | Avena fatua (L.) |
| wild cane | Sorghum bicolor (L). Moench |
| annual ryegrass | Lolium multiflorum (Lam.) |
| milo | Sorghum bicolor (L.) Moench |
| yellow foxtail | Setaria lutescens (Weigle) Hubb. |

The results are shown in Table 11, clearly indicating a marked improvement in the herbicidal efficacy of the herbicide/antidote combination three weeks after application, by the inclusion of the extender compound.

TABLE 11

Herbicidal Activity

| | |
|---|---|
| Herbicide: | S-Ethyl di-n-propylthiocarbamate |
| Antidote: | 2,2,5-Trimethyl-N-dichloroacetyl oxazolidine |
| Extender: | O,O-Diethyl-O-phenyl phosphorothioate |

| Application Rates (lb/A) | | | Percent Control After 3 Weeks | | | | | |
|---|---|---|---|---|---|---|---|---|
| Herbicide | Antidote | Extender | Water-grass | Wild oats | Wild cane | Rye grass | Milo | Fox-tail |
| 3.0 | 0.125 | — | 0 | 10 | 15 | 85 | 20 | 0 |
| 3.0 | 0.125 | 0.5 | 20 | 45 | 30 | 85 | 30 | 5 |

TABLE 11-continued

| Herbicidal Activity | |
|---|---|
| Herbicide: | S-Ethyl di-n-propylthiocarbamate |
| Antidote: | 2,2,5-Trimethyl-N-dichloroacetyl oxazolidine |
| Extender: | O,O-Diethyl-O-phenyl phosphorothioate |

| Application Rates (lb/A) | | | Percent Control After 3 Weeks | | | | | |
|---|---|---|---|---|---|---|---|---|
| Herbicide | Antidote | Extender | Water-grass | Wild oats | Wild cane | Rye grass | Milo | Fox-tail |
| 6.0 | 0.25 | — | 40 | 55 | 5 | 100 | 15 | 10 |
| 6.0 | 0.25 | 1.0 | 75 | 80 | 75 | 100 | 70 | 25 |
| 12.0 | 0.5 | — | 70 | 80 | 35 | 95 | 45 | 30 |
| 12.0 | 0.5 | 2.0 | 85 | 95 | 90 | 100 | 90 | 70 |

EXAMPLE 6

Further Herbicidal Activity Improvement Tests

The tests outlined in this example are carried out in essentially the same manner as in Example 5. As in Example 5, the soil was pre-treated (1st treatment), to simulate a field with a history of prior treatment with the same herbicides, and then retreated (2nd treatment) with the herbicidal test compositions comprising the herbicide and extender, or the herbicide, extender and antidote, as described in Example 3. The tests are different in that:

(1) the herbicides tested were S-ethyl diisobutyl thiocarbamate and S-propyl N,N-dipropyl thiocarbamate;

(2) the antidote, when employed, was N,N-diallyl dichloroacetamide;

(3) the unantidoted tests with S-ethyl diisobutyl thiocarbamate were carried out in river sand;

(4) when stock solutions were prepared both for soil pre-treatment and retreatment, the appropriate amounts of the formulated test chemicals were added to a mixture of 95 cc of water, 5 cc acetone and two drops of the emulsifier polyoxyethylene (20) sorbitan monolaurate, rather than to 100 cc of water;

(5) pre-treatment in the antidoted treatment series was with S-ethyl diisobutyl thiocarbamate plus N,N-diallyl dichloroacetamide;

(6) some flats were untreated at the time of the first treatment to observe weed control under the same conditions in pre-treated and non-pre-treated cases; and (7) the six grass species tested were the following (five weed species and milo):

| COMMON NAME | SCIENTIFIC NAME |
|---|---|
| watergrass | *Echinochloa crusgalli* (L.) Beauv. |
| green foxtail | *Setaria viridis* (L.) Beauv. |
| wild cane | *Sorghum bicolor* (L.) Moench |
| Johnsongrass | *Sorghum halepense* (L.) Pers. |
| wild oats | *Avena fatua* (L.) |
| milo | *Sorghum bicolor* (L.) Moench |

The results as shown in Tables 12, 13, and 14 clearly show that O,O-diethyl-O-phenyl phosphorothioate increased the herbicidal activity of both S-ethyl diisobutylthiocarbamate, antidoted or not, and S-propyl N,N-dipropylthiocarbamate.

TABLE 12

| HERBICIDAL ACTIVITY | |
|---|---|
| Herbicide | S-ethyl N,N-diisobutyl thiocarbamate |
| Extender | O,O-diethyl-O-phenylphosphorothioate |
| Rating | 22 days after 2nd treatment |
| Weeks Between Treatments | 4 |

| Application Rates: lb/A | | | Average % |
|---|---|---|---|
| 1st Treatment | 2nd Treatment | | Control of 6 |
| Herbicide | Herbicide | Extender | Grasses Tested |
| 0 | 0 | 0 | 0% |
| 0 | 3 | 0 | 99.7% |
| 3 | 3 | 0 | 69.5% |
| 3 | 3 | 0.5 | 99.7% |
| 3 | 3 | 1 | 100.0% |

TABLE 13

| HERBICIDAL ACTIVITY | |
|---|---|
| Herbicide: | S-ethyl N,N-diisobutyl thiocarbamate |
| Antidote: | N,N-diallyl dichloroacetamide |
| Extender: | O,O diethyl-O-phenyl phosphorothioate |
| Rating: | 14 days after 2nd treatent |
| Weeks Between Treatments: | 6 |

| Application Rates lb/A | | | | | |
|---|---|---|---|---|---|
| 1st Treatment | | 2nd Treatment | | | Average % Control |
| Herbicide | Antidote | Herbicide | Antidote | Extender | of 6 Grass Species |
| 0 | 0 | 0 | 0 | 0 | 0 |
| 0 | 0 | 3 | 0.167 | 0 | 82.3 |
| 3 | 0.167 | 3 | 0.167 | 0 | 16 |
| 3 | 0.167 | 3 | 0.167 | 1 | 87.5 |

TABLE 14

| HERBICIDAL ACTIVITY | |
|---|---|
| Herbicide: | S-propyl N,N-dipropyl thiocarbamate |
| Antidote: | N,N-diallyl dichloroacetamide |
| Extender: | O,O-diethyl-O-phenyl phosphorothioate |
| Rating: | 14 days after 2nd treatment |

TABLE 14-continued

| HERBICIDAL ACTIVITY | | | | | |
|---|---|---|---|---|---|
| Application Rates lb/A | | | | | |
| 1st Treatment | | 2nd Treatment | | | Average % Control |
| Herbicide | Antidote | Herbicide | Antidote | Extender | of 6 Grass Species |
| 0 | 0 | 0 | 0 | 0 | 0 |
| 0 | 0 | 3 | 0.25 | 0 | 79.3 |
| 3 | 0.25 | 3 | 0.25 | 0 | 8.3 |
| 3 | 0.25 | 3 | 0.25 | 1 | 78.8 |

EXAMPLE 7

Further Herbicidal Activity Improvement Tests

This example again shows herbicidal activity test data indicating the effectiveness of the extender compounds in improving the herbicidal activity of thiocarbamates. The effect is observed by comparing the extent of weed control in test flats treataed with a thiocarbamate against that occurring in similar flats treated with both the thiocarbamate and the extender. The soil used in these tests was a sandy loam soil from San Jose, Calif., which was pre-treated with the herbicide to simulate a typical field which had received previous herbicide applications.

A. Soil Pre-Treatment

A solution was prepared by diluting an emulsifiable liquid concentrate containing either 6 lb/gal (0.72 kg/l) (75% by weight) of the herbicide S-ethyl N,N-diisobutyl thiocarbamate in 200 ml of water, such that the resulting concentration of herbicide in the solution was 2000 mg/l. Two hundred ml of this solution was then added to 200 lb (90.8 kg) of soil and the mixture was mixed in a rotary mixer for thirty minutes. Also added was 17-17-17 fertilizer (N-$P_2O_5$-$K_2O$ on a weight basis), amounting to 50 ppm by weight with respect to the soil.

The soil was then placed in round plastic containers, 7.5 inches (19.0 cm) in diameter by 7.5 inches (19.0 cm) deep. The soil was tamped and leveled with a row marker to impress three rows across the width of each container. One row was seeded with DeKalb XL-45A corn (*Zea mays*), and two rows were seeded with barnyardgrass (*Echinochloa crus-galli*). Sufficient seeds were planted to produce several seedlings per row. The containers were then placed in a greenhouse maintained at 20° C. to 30° C. and watered daily by sprinkler.

Five weeks after treatment, the soil was allowed to dry out and the plant foliage was removed. The soil was then passed through a 0.25 inch (0.64 cm) screen to remove plant roots and clods, and then passed through a 2 millimeter (mm) screen.

B. Herbicide Test

A thiocarbamate preparation described in Part A was used. The extender compounds were used in technical form. These materials were added to 100 cc mixtures of equal parts of water and acetone at such amounts that 5 cc of the resulting mixture when added to three pounds of soil yielded a quantity in the soil equivalent to the desired application rate expressed in pounds per acre. Thus, 5 cc of the mixture and three pounds of soil were placed in a rotary mixer.

The treated soil was then placed in aluminum flats which were 3 inches deep, 4 inches wide, and 8 inches long (7.6×10.2×20.3 cm). The soil was tamped and leveled with a row marker to impress six rows across the width of the flat. The test weeds were as follows:

| COMMON NAME | SCIENTIFIC NAME |
|---|---|
| watergrass | *Echinochloa crus-galli* (L.) |
| milo | *Sorghum bicolor* (L.) Moench |
| wild oats | *Avena fatua* (L.) |
| wild cane | *Sorghum bicolor* (L.) Moench |
| yellow foxtail | *Setaria lutescens* (Weigle) Hubb. |

DeKalk XL-45A corn of species *Zea mays* (L.) was also planted.

Sufficient seeds were planted to produce several seedlings per inch in each row. The flats were then placed in a greenhouse maintained at 70° to 85° F. (21° to 30° C.) and watered daily by sprinkler.

Approximately three weeks after treatment, the degree of weed control and corn injury were estimated and recorded as percentage control compared to the growth of the same species in an untreated check flat of the same age. The rating scale ranges from 0 to 100%, where 0 equals no effect with plant growth equal to the untreated control, and 100 equals complete kill.

The results are listed in Tables 15 and 16 each representing a separate batch of tests. Control experiments (with no extender present) were included in each batch for comparison. Substantial improvements in average percent weed control over the control experiments are evident. The herbicidal efficacy of the thiocarbamate three weeks after application was much improved by the use of the extender, whereas the corn remained unaffected.

TABLE 15

| HERBICIDAL ACTIVY TEST | |
|---|---|
| Herbicide: | S-ethyl N,N-diisobutyl thiocarbamate at 3 lb/A |
| Soil: | San Jose sandy loam soil pre-treated with S-ethyl diisobutyl thiocarbamate at 3 lb/A |
| Extender: | As shown, at application rate shown |
| Evaluation Time: | 20 days after re-treatment |

| Extender | Application Rate lb/A | Water grass | Wild cane | Wild oats | Yellow foxtail | Milo | Corn | Average % Control of 1st 5 Grasses |
|---|---|---|---|---|---|---|---|---|
| None (ave. of 2) | — | 35 | 20 | 40 | 3 | 33 | 0 | 26 |

TABLE 15-continued

| HERBICIDAL ACTIVY TEST | | | | | | | | |
|---|---|---|---|---|---|---|---|---|
| O,O-diethyl- | 1 | 90 | 100 | 100 | 65 | 100 | 0 | 91 |
| O-phenyl | 2 | 80 | 100 | 100 | 70 | 100 | 0 | 90 |
| phosphoro-thioate | 3 | 75 | 100 | 95 | 70 | 95 | 0 | 87 |
| O,O-diethyl- | 1 | 75 | 100 | 100 | 80 | 100 | 0 | 91 |
| O-benzyl | 2 | 85 | 100 | 95 | 85 | 100 | 0 | 93 |
| phosphoro-thioate | 3 | 75 | 95 | 95 | 50 | 95 | 0 | 82 |
| O-ethyl- | 1 | 85 | 95 | 100 | 85 | 95 | 0 | 92 |
| S-ethyl-O- | 2 | 85 | 95 | 95 | 80 | 100 | 0 | 91 |
| phenyl phos-phorothioate | 3 | 80 | 95 | 95 | 80 | 100 | 0 | 90 |

TABLE 16

HERBICIDAL ACTIVY TEST

| | |
|---|---|
| Herbicide: | S-ethyl N,N-diisobutyl thiocarbamate at 3 lb/A |
| Soil: | San Jose sandy loam soil pre-treated with s-ethyl diisobutyl thiocarbamate at 6 lb/A |
| Extender: | As shown, at application rate shown |
| Evaluation Time: | 21 days after re-treatment |

| Extender | Application Rate lb/A | Water grass | Wild cane | Wild oats | Yellow foxtail | milo | 45A corn | Average % Control of 1st 5 Grasses |
|---|---|---|---|---|---|---|---|---|
| None (ave. of 2) | — | 90 | 90 | 48 | 88 | 75 | 0 | 78 |
| O,O-diethyl- | 1 | 85 | 100 | 95 | 90 | 100 | 0 | 94 |
| O-phenyl | 2 | 85 | 100 | 95 | 90 | 100 | 0 | 94 |
| phosphoro-thioate | 3 | 70 | 95 | 100 | 75 | 100 | 0 | 88 |
| O,O-diethyl- | 1 | 85 | 100 | 95 | 90 | 95 | 0 | 93 |
| O-benzyl | 2 | 85 | 100 | 95 | 90 | 100 | 0 | 94 |
| phosphoro-thioate | 3 | 90 | 100 | 100 | 90 | 100 | 0 | 96 |
| O-ethyl- | 1 | 90 | 95 | 100 | 95 | 100 | 0 | 96 |
| S-ethyl-O- | 2 | 90 | 100 | 100 | 95 | 100 | 0 | 97 |
| phenyl phos-phorothioate | 3 | 95 | 100 | 100 | 100 | 100 | 0 | 99 |

EXAMPLE 8

Components of Two- and Three- Component Compositions Tested Alone and in Combinations The following chemicals, alone and in combination, were pre-plant incorporated in San Jose sandy loam soil which had no previous history of thiocarbamate herbicide treatment according to the method of Example 3 with proviso (4) of Example 6:

(1) S-ethyl N,N-dipropyl thiocarbamate at 3 lb/A;
(2) N,N-diallyl dichloroacetamide at 0.25 lb/A;
(3) O,O-diethyl-O-phenyl phosphorothioate at 2 or 4 lb/A;
(4) S-ethyl N,N-dipropyl thiocarbamate at 3 lb/A+N,N-diallyl dichloroacetamide at 0.25 lb/A; and
(5) S-ethyl N,N-dipropyl thiocarbamate at 3 lb/A+N,N-diallyl dichloroacetamide at 0.25 lb/A+O,O-diethyl-O-phenyl phosphorothioate at 2 and 4 lb/A.

The soil was placed in flats and planted with one row of DeKalb XL-43A corn seeds and with rows of the 6 grass species named above in Example 6.

The flats were placed in the greenhouse at 70°-90° F. and watered as needed. The results taken 17 days after treatment are shown in Table 17. The results indicate that S-ethyl N,N-dipropyl thiocarbamate alone injured corn whereas the antidote N,N-diallyl dichloroacetamide and the extender O,O-diethyl O-phenyl phosphorothioate when tested individually neither injured corn nor had any herbicidal activity. When S-ethyl N,N-dipropyl thiocarbamate and the antidote N,N-diallyl dichloroacetamide were tested in combination, there was no injury to corn. S-ethyl N,N-dipropyl thiocarbamate when tested along gave 98.5% control of the weeds, and this degree of weed control did not change significantly when either N,N-diallyl dichloroacetamide or O,O-diethyl-O-phenyl phosphorothioate were added either alone or in combination.

TABLE 17

COMPARATIVE SERIES OF BIOASSAY TESTS WITH COMPONENTS OF COMPOSITIONS, ALONE AND IN COMBINATION

| | |
|---|---|
| Herbicide: | S-ethyl N,N-dipropyl thiocarbamate |
| Antidote: | N,N-diallyl dichloroacetamide |
| Extender: | O,O-diethyl-O-phenyl phosphorothioate |
| Rating: | 17 days after treatment |

| Application Rates lb/A | | | % Corn Twisting Injury | Average % Control of 6 Grass Species |
|---|---|---|---|---|
| Herbicide | Antidote | Extender | | |
| 0 | 0 | 0 | 0 | 0 |
| 3 | 0 | 0 | 30 | 98.5 |
| 0 | 0.25 | 0 | 0 | 0 |
| 0 | 0 | 2 | 0 | 0 |
| 0 | 0 | 4 | 0 | 0 |
| 3 | 0.25 | 0 | 0 | 95.5 |
| 3 | 0 | 2 | 35 | 98.5 |
| 3 | 0.25 | 2 | 0 | 98.2 |
| 3 | 0.25 | 4 | 0 | 98.0 |

EXAMPLE 9

Further Herbicidal Activity Improvement Tests with Three-Component Compositions Further tests were carried out to show that a representative extender of the instant invention acts to extend the soil life of herbicidal compositions containing a representative thiocarbamate and representative antidotes.

The soil for most flats was pre-treated (1st treatment) and then retreated (2nd treatment) as in Examples 5, 6, 7 and 8. The soil for one flat, however, was not pretreated and was treated with thiocarbamate for the first time at the time the other flats were being retreated. All the flats except that one flat, upon second treatment, were treated with test compositions comprising a thiocarbamate herbicide, a thiocarbamate and antidote, a thiocarbamate and an antidote, or a thiocarbamate, antidote and an extender, essentially as described in Example 3. The second treatment differed from the described in Example 3 in that:

1. the aluminum flats were 3 inches (7.6 cm) deep, 6 inches (15.24 cm) wide, and 8 inches (20.32 cm) long;

2. the antidote stock solutions were prepared by dissolving 37 mg of each antidote (technical grade) in 5 ml of acetone and then adding 0.1 ml of a blend of polyoxyethylene ethers of sorbitan monolaurate as an emulsifier and 95 ml of water;

3. 10 ml of the thiocarbamate stock solution was mixed with 10 ml of the antidote stock solution and, in some cases, with 10 ml of the extender stock solution;

4. one row each of the following grass species were planted:

| Commn Name | Scientific Name |
|---|---|
| green foxtail | *Setaria viridis* |
| watergrass | *Echinochloa crus-galli* |
| wild cane | *Sorghum bicolor;* | and 5. also planted in each flat three rows were planted with DeKalb Xl-64 corn of species *Zea mays* (L.)

The flats were placed in the greenhouse at 70°–90° F. and watered lightly as needed.

The flats were rated 3 weeks after the second treatment. Table 18 indicates the antidotes tested. There was no indication of any herbicidal injury to any of the rows of corn in any flat, so those results are not recorded below in Table 19. The tabulated results indicate that the extender restored the herbicidal activity of the thiocarbamate alone or thiocarbamate and antidote compositions in soil which had been pretreated with the herbicide.

TABLE 18

| Antidote Compound No. | Antidotes Tested — Structure |
|---|---|
| 1 | Cl$_2$CHC(O)N(C$_2$H$_5$)(CH$_2$–C$_6$H$_5$) |
| 2 | Cl$_2$CHC(O)N(CH$_2$CH=CH$_2$)(CH$_2$CH(OCH$_3$)$_2$) |
| 3 | Cl$_2$CHC(O)N–CH$_2$CH$_2$–C(CH$_3$)$_2$–S (ring) |
| 4 | Cl$_2$CHC(O)N–CH$_2$CH$_2$(C$_6$H$_5$)–C(CH$_3$)$_2$–O (ring) |
| 5 | Cl$_2$CHC(O)N–CH$_2$–CH=CH$_2$, with dioxolane ring |

TABLE 19

Herbicidal Activity Test

| | |
|---|---|
| Herbicide: | EPTAM ® = S-ethyl N,N-di-n-propyl thiocarbamate |
| Antidote Nos.: | Keyed to Table 18 |
| Extender: | O,O-diethyl-O-phenyl phosphorothioate |
| Evaluation Time: | Three weeks after 2nd treatment |
| Application Rate: | As shown |

| | Second Treatment (6 Weeks After the First) | | | % Control of Weeds 3 Weeks After Second Treatment | | |
|---|---|---|---|---|---|---|
| 1st Treatment EPTAM ® lb/A | EPTAM lb/A | Antidote at 1 lb/A | Extender lb/A | Water grass | Green Foxtail | Wild Cane |
| 0 | 0 | 0 | 0 | 0 | 0 | 0 |
| 0 | 3 | 0 | 0 | 94 | 95 | 98 |
| 3 | 3 | 0 | 0 | 0 | 0 | 3 |
| 3 | 3 | 0 | 4 | 96 | 85 | 97 |
| 3 | 3 | 1 | 0 | 0 | 0 | 0 |
| 3 | 3 | 1 | 4 | 95 | 75 | 95 |
| 3 | 3 | 2 | 0 | 0 | 0 | 0 |
| 3 | 3 | 2 | 4 | 97 | 80 | 98 |
| 3 | 3 | 3 | 0 | 0 | 0 | 0 |
| 3 | 3 | 3 | 4 | 70 | 80 | 92 |
| 3 | 3 | 4 | 0 | 0 | 0 | 0 |

TABLE 19-continued

| | | | | Herbicidal Activity Test | | |
|---|---|---|---|---|---|---|
| 3 | 3 | 4 | 4 | 97 | 80 | 90 |
| 3 | 3 | 5 | 0 | 0 | 0 | 0 |
| 3 | 3 | 5 | 4 | 98 | 85 | 100 |

EXAMPLE 10

Tests with Extender in Pretreated Soil

The extender O,O-diethyl O-phenyl phosphorothioate was tested alone at 4 and 8 lb/A in soil pretreated with a thiocarbamate. This example differs from that of Example 8 where the extender was tested alone at 2 and 4 lb/A in non-conditioned soil, meaning the soil had not been pretreated.

These tests were run concurrently with those recorded in Example 9. The same procedures were followed except that only 10 ml of the extender alone was incorporated into the soil pretreated with EPTAM® six weeks earlier.

The results, recorded in Table 20, indicate that at 4 and 8 lb/acre the extender exhibited no herbicidal activity whatsoever in soil pretreated with EPTAM®.

TABLE 20

Herbicidal Activity Test - Extender Alone

| Extender: | O,O-diethyl O-phenyl phosphorothioate |
|---|---|
| Application Rate: | 4 and 8 lb/A |
| Evaluation Time: | Three weeks after 2nd treatment |

| | Second Treatment 6 Weeks After the First | | | | | % Control of Weeds 3 Weeks After Second Treatment | | |
|---|---|---|---|---|---|---|---|---|
| 1st Treatment EPTAM ® lb/A | EPTAM lb/A | + | Antidote at 1 lb/A | + | Extender lb/A | Water grass | Green Foxtail | Wild Cane |
| 0 | 0 | | 0 | | 0 | 0 | 0 | 0 |
| 3 | 0 | | 0 | | 4 | 0 | 0 | 0 |
| 3 | 0 | | 0 | | 8 | 0 | 0 | 0 |

EXAMPLE 11

Herbicidal Activity of Several Different Thiocarbamates

This example provides data much like that of Example 10 above, and essentially follows the procedures therein described. Sandy loam soil from San Jose, Calif. was used in these tests. It was pretreated to simulate previous herbicide applications.

The thiocarbamate herbicide which was tested according to the procedure described below was S-ethyl-N-ethyl-N-cylohexyl thiocarbamate (RO-NEET®).

A: Soil Pre-Treatment

A stock solutions of the thiocarbamate herbicide was prepared as follows: 149.4 mg of an emulsifiable liquid concentrate of RO-NEET® containing 6 lb/gal (0.72 kg/l) (74.3% by weight of the herbicide) was suspended as an emulsion in 100 ml of water.

The sandy loam soil was measured out to fill aluminum flats 8.5×6.0×1.75 inches (22×15×4.5 cms). The soil was then emptied from each flat individually into a 5-gallon rotary mixer. Ten ml of the thiocarbamate stock solution was then pipetted and placed into the rotary mixer where it was incorporated. The soil was then replaced in the flat. The application rate provided by 10 ml was calculated as 3 lb/A of the herbicide.

Each flat was then planted with two rows of watergrass (*Echinochloa crus-galli*) and one row each of johnsongrass (*Sorghum haliepense*), wild oats (*Avena fatua*) and milo (*Sorghum bicolor*). The flats were placed in the greenhouse at 70°–95° F. and watered daily by sprinkling.

Two months later, the plants and roots were removed by sieving. The soil was replaced in the flats.

B. Herbicide Test

The RO-NEET® stock solution preparation described in Part (A) was formulated again. An additional stock solution of the organophosphorus extender compound was prepared as follows:

38.7 mg of technical grade, O,O-diethyl-O-phenyl phosphorothioate was combined with 5 cc of acetone, 95 ml of water, and 0.2 ml of an emulsifier/surfactant. Ten ml of the last stock solution translated to 1 lb/A when applied to a flat of soil.

Two flats as in Part (A) above were filled with soil treated as in Part (A). Incorporated into one flat's worth of pretreated soil by rotary mixing was a 20 ml tank-mix comprising 10 ml of the RO-NEET® stock solution and 10 ml of the extender stock solution. Incorporated into another flat's worth of pretreated soil was just 10 ml of RO-NEET® stock solution alone.

Incorporated into the flat of non-pretreated soil was 10 ml of the RO-NEET® stock solution. One flat of non-pretreated soil was left untreated at the time for second soil treatment as an untreated control flat.

The weed control ratings, measured as in Example 1 above, were taken 15 days after the second treatment and are recorded in Table 22 below. The results show that adding the representative organophosphorus extender O,O-diethyl-O-phenyl-phosphorothioate extended the herbicidal activity of RO-NEET® when tested upon re-treatment. An untreated control flat provides the first line of data in Table 22.

TABLE 22

Herbicidal Activity of Several different thiocarbamates Improved by the Extender: O,O-diethyl O-phenyl phosphorothioate Application Rate: As indicated in terms of lb/A

TABLE 22-continued

Herbicidal Activity of Several different thiocarbamates Improved by the Extender: O,O-diethyl O-phenyl phosphorothioate Application Method: Pre-plant incorporation

| First Soil Treatment | | Second Soil Treatment, PPI* | | | | | | |
|---|---|---|---|---|---|---|---|---|
| | | Herbicide | lb/A | Extender lb/A | Water grass* | Wild cane | Johnson grass | Wild oats | Sorghum |
| | 0 | 0 | 0 | 0 | 0 | 0 | 0 | 0 | 0 |
| | 0 | RO-NEET | 3 | 0 | 83 | 75 | 90 | 100 | 75 |
| RO-NEET | 3 | RO-NEET | 3 | 0 | 73 | 30 | 20 | 85 | 10 |
| RO-NEET | 3 | RO-NEET | 3 | 1 | 81 | 90 | 100 | 100 | 97 |

*Results shown for watergrass are an average of two replications.

EXAMPLE 12

Further Tests Indicating Herbicidal Activity Improvement with Herbicide, Extender and Antidote Compositions This example offers herbicidal activity test data demonstrating the effectiveness of representative organophosphorus extender compounds in prolonging the herbicidal activity of compositions containing a thiocarbamate herbicide and a representative antidote of the instant invention. The effect is observed by comparing the extent of weed control in test flats treated with a thiocarbamate and antidote composition only against the weed control occurring in similar flats treated with compositions containing a thiocrbamate herbicide, an antidote and an organophosphorus extender. The soil used in these tests was a sandy loam soil from San Jose, Calif., which was pre-treated with a thiocarbamate herbicide to simulate a typical field which had received previous herbicide applications.

A. Soil Pre-Treatment

A solution was prepared by diluting an emulsifiable liquid concentrate containing 6 lb/gal (0.72 kg/l) (76.8% by weight) of the herbicide S-ethyl di-n-propylthiolcarbamate in 200 ml of water, such that the resulting concentration of herbicide in the solution was 2000 mg/l. Two hundred ml of this solution was then added to 200 lb (90.8 kg) of soil and the mixture was mixed in a rotary mixer for thirty minutes. Also added was 17-17-17 fertilizer (N-P$_2$O$_5$-K$_2$O on a weight basis), amounting to 50 ppm by weight with respect to the soil.

The soil was then placed in round plastic containers, 7.5 inches (19.0 cm) in diameter by 7.5 inches (19.0 cm) deep. The soil was tamped and leveled with a row marker to impress three rows across the width of each container. One row was seeded with DeKalb XL-45A corn (*Zea mays*), and two rows were seeded with barnyardgrass (*Echinochloa crus-galli*). Sufficient seeds were planted to produce several seedlings per inch of row. The containers were then placed in a greenhouse maintained at 20° C. to 30° C. and watered daily by sprinkler.

Five weeks after treatment, the soil was allowed to dry out and the plant foliage was removed. The soil was then passed through a 0.25 inch (0.64 cm) screen to remove plant roots and clods, and then passed through a 2 millimeter (mm) screen.

B. Herbicide Test

Stock solutions for the tests recorded in Table 23 were prepared by adding to 100 cc of water such amounts of emulsifiable liquid concentrates of an organophosphorus extender compound or of a composition comprising a thiocarbamate herbicide and a representative antidote of the instant invention such that 5 cc of the resulting mixture when added to three pounds of soil yielded a quantity of soil equivalent to the desired application rate expressed in pounds per acre. Stock solutions for the tests recorded in Table 24 were prepared as just indicated and in addition another stock solution was prepared by adding such amounts of a technical grade organophosphorus extender compound to 100 cc mixture of equal parts of water and acetone such that 5 cc of the resulting mixture when added to three pounds of soil would also yield the desired application rate. Then either 5 cc of a stock solution containing a thiocarbamate herbicide and an antidote or 10 cc of a tank-mix comprising 5 cc of the thiocarbamate and antidote stock solution and 5 cc of an organophosphorus extender stock solution were incorporated into three pounds of soil in a rotary mixer.

The treated soil was then placed in aluminum flats which were approximately 3 inches deep, 6 inches wide and 9 inches long (8×15×23 cm). The soil was tamped and leveled with a row marker to impress six rows across the width of the flat. The test weeds employed in the tests recorded in Table 23 were as follows:

| COMMON NAME | SCIENTIFIC NAME |
|---|---|
| watergrass | *Echinochloa crus-galli* (L.) |
| wild oats | *Avena fatua* (L.) |
| wild cane | *Sorghum bicolor* (L.) Moench |
| green foxtail | *Setaria viridis* (L.) Beauv. |

The same weed species were employed in the tests recorded in Table 24 with the addition of annual ryegrass (*Lolium multiflorum*). In both series of tests, milo [(*Sorghum bicolor* (L.) Moench] was included as a plant growth indicator.

Sufficient seeds were planted to produce several seedlings per inch in each row. The flats were then placed in a greenhouse maintained at 70° to 85° F. (21° to 30° C.) and watered daily by sprinkler.

Approximately three weeks after treatment, the degree of weed control and corn injury were estimated and recorded as percentage control compared to the growth of the same species in an untreated check flat of the same age. The rating scale ranges from 0 to 100%, where 0 equals no effect with plant growth equal to the untreated control, and 100 equals complete kill.

The thiocarbamates tested were as follows:
EPTAM=S-ethl-N,N-dipropyl thiocarbamate
SUTAN=S-ethyl-N,N-diisobutyl thiocarbamate
VERNAM=S-propyl-N,N-dipropyl thiocarbamate
The antidotes tested were:
A-1=N,N-diallyl-dichloroacetamide
A-2=2,2,5-trimethyl-N-dichloroacetyl oxazolidine The organophosphorus extender compounds tested were:
Ex-1=O,O-diethyl-O-phenyl phosphorothioate
EX-2=O,O-diethyl-O-benzyl phosphorothioate.

Table 23 and Table 24 indicate that representative organophosphorus extender compounds prolong the herbicidal activity of thiocarbamate herbicide compositions containing a representative antidoate.

TABLE 23
Herbicidal Activity Tests of 3-Component Compositions

Antidote: A-2 = 2,2,5-Trimethyl N-dichloroacetyl oxazolidine
Extender: EX-1 = O,O-Diethyl-O-phenyl phosphorothioate

TREATMENT

| Herbicide | Application Rate (lb/A) | Antidote | Application Rate (lb/A) | Extender | Application Rate (lb/A) | Ave. % Control |
|---|---|---|---|---|---|---|
| 1. SUTAN | 3.0 | A-2 | 0.06 | — | — | 33% |
| 2. SUTAN | 6.0 | A-2 | 0.12 | — | — | 42% |
| 3. SUTAN | 3.0 | A-2 | 0.06 | EX-1 | 0.50 | 75% |
| 4. SUTAN | 6.0 | A-2 | 0.12 | EX-1 | 1.00 | 88% |
| 5. EPTAM | 3.0 | A-2 | 0.12 | — | — | 6% |
| 6. EPTAM | 6.0 | A-2 | 0.25 | — | — | 12% |
| 7. EPTAM | 3.0 | A-2 | 0.12 | EX-1 | 0.50 | 34% |
| 8. EPTAM | 6.0 | A-2 | 0.25 | EX-1 | 1.00 | 47% |
| 9. VERNAM | 3.0 | A-2 | 0.12 | — | — | 5% |
| 10. VERNAM | 6.0 | A-2 | 0.25 | — | — | 23% |
| 11. VERNAM | 3.0 | A-2 | 0.12 | EX-1 | 0.50 | 78% |
| 12. VERNAM | 6.0 | A-2 | 0.25 | EX-1 | 1.00 | 93% |

TABLE 24
Further Herbicidal Activity Tests of 3-Component Compositions

Antidote: A-1 = N,N-diallyl dichloroacetamide
Extender: EX-2 = O,O-Diethyl-O-benzyl phosphorothioate

TREATMENT

| Herbicide | Application Rate (lb/A) | Antidote | Application Rate (lb/A) | Extender | Application Rate (lb/A) | Ave. % Control |
|---|---|---|---|---|---|---|
| 1. EPTAM | 3.0 | A-1 | 0.25 | — | — | 3% |
| 2. EPTAM | 6.0 | A-1 | 0.50 | — | — | 73% |
| 3. EPTAM | 3.0 | A-1 | 0.25 | EX-2 | 0.50 | 88% |
| 4. EPTAM | 3.0 | A-1 | 0.25 | EX-2 | 0.50 | 80% |
| 5. EPTAM | 6.0 | A-1 | 0.50 | EX-2 | 1.00 | 90% |
| 6. EPTAM | 6.0 | A-1 | 0.50 | EX-2 | 1.00 | 91% |
| 7. SUTAN | 3.0 | A-1 | 0.125 | — | — | 69% |
| 8. SUTAN | 6.0 | A-1 | 0.25 | — | — | 95% |
| 9. SUTAN | 3.0 | A-1 | 0.125 | EX-2 | 0.50 | 100% |
| 10. SUTAN | 3.0 | A-1 | 0.125 | EX-2 | 0.50 | 99% |
| 11. SUTAN | 6.0 | A-1 | 0.25 | EX-2 | 1.00 | 100% |
| 12. SUTAN | 6.0 | A-1 | 0.25 | EX-2 | 1.00 | 100% |

EXAMPLE 13
Further Herbicidal Activity Tests of 3-Component Compositions

Further tests comparing the herbicidal activity of thiocarbamate herbicide and dihaloacetamide antidote compositions in soil preteated with a thiocarbamate and the herbicidal activity of such compositions also comprising an extender were conducted according to the following procedures. These tests were similar to those of Example 7 except that they were run at different application rates of the components. The weight ratio of thiocarbamate to the antidote herein is 12:1. The weight ratio of the thiocarbamate to the extender herein is 6:1.

The following two antidotes were employed in these tests:

Antidote Compound No. 5 (structure in Table 18 above)=N-allyl-N-[2-(1,3-dioxolanyl)]-methyl dichloroacetamide;

Antidote Compound No. 6=N,N-diallyl dichloroacetamide

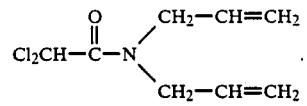

A. Soil Pre-Treatment

The same procedure as in Example 7, Part (A) was employed. The soil was thereby pretreated with S-ethyl N,N-di-n-propyl thiocarbamate at 3 lb/A.

B. Herbicide Test

The following stock solutions were prepared:

1. 120 mg of technical grade S-ethyl N,N-di-n-propyl thiocarbamate was dissolved in 50 ml of water and 50 ml of acetone such that 6.7 ml of the resulting mixture when added to three pounds of soil yielded an application rate of 4 lb/acre;

2. 144 mg of an emulsifiable concentrate containing 83% S-ethyl N,N-di-n-propyl thiocarbamate and 6.9% N,N-diallyl dichloroacetamide (hereinafter Antidote #6) was dissolved in 100 ml of water such that 6.7 ml when combined with 3 pounds of soil yielded an application rate of 4 lb/Acre of the herbicide and 0.3 lb/A of the antidote;

3. 60 mg of technical grade N-allyl-N-[2-(1,3-dioxolanyl)]methyl dichloroacetamide (hereinafter Antidote #5) was dissolved in 50 ml of acetone and 50 ml of water such that 1.3 ml combined with 3 pounds of soil yielded an application rate of 0.3 lb/A;

4. 108 mg of technical grade O,O-diethyl O-phenyl phosphorothioate was dissolved in 50 ml of acetone and 50 ml of water such that 1.3 ml when combined with 3 pounds of soil yielded an application rate of 0.67 lb/A.

Apporopriate amounts of the stock solutions were then incorporated in the soil either alone or in a tank-mix with other components depending on the treatment for the particular flat.

The treated soil was then placed in aluminum flats which were 2.5 inches deep, 3.5 inches wide and 7.5 inches long (6.4×8.9×19.0 cm). The soil was tamped and leveled with a row marker to impress six rows across the width of the flat.

The same weed species and plant growth indicators as used in Example 7 above were employed except green foxtail (*Setaria viridis*) was employed rather than yellow foxtail.

The flats were then placed in a greenhouse maintained at 70° to 85° F. and watered daily by sprinklers. The visual weed control ratings were taken two weeks after the intial treatment.

The results recorded in Table 25 are each the average of two replications except for results asterisked (*) indicating an average of four replications. The results show that the addition of a representative extender to a thiocarbamate and herbicide composition extends the herbicidal activity of such compositions.

TABLE 25

Further Herbicidal Activity Tests of 3-Component Compositions

| Herbicide: | S-ethyl N,N-di-n-propyl thiocarbamate (EPTAM ®) |
| Antidote: | A-5 = N-allyl-N-[2-(1,3-dioxolanyl)]-methyl dichloroacetamide |
| | A-6 = N,N-diallyl dichloroacetamide |
| Extender: | O,O-diethyl-O-phenyl phosphorothioate |
| Evaluation: | 3 weeks after treatment |
| Soil Pretreatment: | 3 lb EPTAM ® |

| Treatment | | | | |
| --- | --- | --- | --- | --- |
| EPTAM ® Application Rate (lb/A) | Antidote | Application Rate (lb/A) | Extender Application Rate (lb/A) | Avg. % Control |
| 0 | A-5 | 0.3 | 0 | 0 |
| 0 | A-5 | 0.5 | 0 | 0 |
| 0 | A-5 | 0.7 | 0 | 0 |
| 4 | A-5 | 0.3 | 0 | 12* |
| 6 | A-5 | 0.5 | 0 | 36* |
| 9 | A-5 | 0.7 | 0 | 50.5* |
| 4 | A-5 | 0.3 | 0.67 | 34 |
| 6 | A-5 | 0.5 | 1.0 | 62 |
| 9 | A-5 | 0.7 | 1.5 | 78 |
| 4 | A-6 | 0.3 | 0 | 0 |
| 6 | A-6 | 0.5 | 0 | 23 |
| 9 | A-6 | 0.7 | 0 | 26 |
| 4 | A-6 | 0.3 | 0.67 | 27 |
| 6 | A-6 | 0.5 | 1.0 | 72 |
| 9 | A-6 | 0.7 | 1.5 | 77 |

METHODS OF APPLICATION

The herbicidal compositions of the present invention are useful in controlling the growth of undersirable vegetation by pre-emergence or post-emergence application to the locus where control is desired, including pre-plant and post-plant soil incorporation as well as surface application. The compositions are generally embodied in formuations suitable for convenient application. Typical formulations contain additional ingredients or diluent carriers which are either inert or active. Examples of such ingredients or carriers are water, organic solvents, dust carriers, granular carriers, surface active agents, oil and water, water-oil emulsions, wetting agents, dispersing agents, and emulsifying agents. The herbicidal formulations generally take the form of dusts, emulsifiable concentrates, granules and pellets, or microcapsules.

A. DUSTS

Dusts are dense powder compositions which are intended for application in dry form. Dusts are characterized by their free-flowing and rapid settling properties so that they are not readily windborne to areas where their presence is not desired. They contain primarily an active material and a dense, free-flowing, solid carrier.

Their performance is sometimes aided by the inclusion of a wetting agent, and convenience in manufacture frequently demands the inclusion of an inert, absorptive grinding aid. For the dust compositions of this invention, the inert carrier may be either of vegetable or mineral origin, the wetting agent is preferably anionic or nonionic, and suitable absorptive grinding aids are of mineral origin.

Suitable classes of inert solid carriers for use in the dust compositions are those organic or inorganic powders which possess high bulk density and are very free-flowing. They are also characterized by low surface area and poor liquid absorptivity. Suitable grinding aids are natural clays, diatomaceous earth, and synthetic mineral fillers derived from silica or silicate. Among ionic and nonionic wetting agents, the most suitable are the members of the group known to the art as wetting agents and emulsifiers. Although solid agents are preferred because of ease in incorporation some liquid nonionic agents are also suitable in the dust formulation.

Preferred dust carriers are micaceous talcs, pyrophyllite, dense kaolin clays, tobacco dust and ground calcium phosphate rock.

Preferred grinding aids are attapulgite clay, diatomaceous silica, synthetic fine silica and synthetic calcium and magnesium silicates.

Most preferred wetting agents are alkylbenzene and alkylnaphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, and ditertiary acetylenic glycols. Preferred dispersants are methyl cellulose, polyvinyl alcohol, lignin sulfonates, polymeric alkylnaphthalene sulfonates, sodium naphthalenesulfonate, polymethylene bisnaphthalenesulfonate, and sodium-N-methyl-N-(long chain acid) taurates.

The inert solid carriers in the dusts of this invention are usually present in concentrations of from about 30 to 90 weight percent of the total composition. The grinding aid will usually constitute 5 to 50 weight percent of the compositions, and the wetting agent will constitute from about 0 to 1.0 weight percent of the composition. Dust compositions can also contain other surfactants such as dispersing agents in concentrations of up to about 0.5 weight percent, and minor amounts of anticaking and antistatic agents. The particle size of the carrier is usually in the range of 30 to 50 microns.

B. EMULSIFIABLE CONCENTRATE

Emulsifiable concentrates are usually solutions of the active materials in nonwater-miscible solvents together with an emulsifying agent. Prior to use, the concentrate is diluted with water to form a suspended emulsion of solvent droplets.

Typical solvents for use in emulsifiable concentrates include weed oils, chlorinated hydrocarbons, and non-water-miscible ethers, esters, and ketones.

Typical emulsifying agents are anionic or nonionic surfactants, or mixtures of the two. Examples inlcude long-chain alkyl or mercaptan polyethoxy alcohols, alkylaryl polyethoxy alcohols, sorbitan fatty acid esters, polyoxyethylene ethers with sorbitan fatty acid esters, polyoxyethylene glycol esters with fatty or rosin acids, fatty alkylol amide condenstes, calcium and amine salts of fatty alcohol sulfates, oil soluble petroleum sulfonates or, preferably mixtures of these emulsifying agents. Such emulsifying agents will comprise from about 1 to 10 weight percent of the total composition.

Thus, emulsifiable concentrates of the present invention will consist of from about 15 to about 50 weight percent active material, about 40 to 82 weight percent solvent, and about 1 to 10 weight percent emulsifier. Other additivies such as spreading agents and stickers can also be included.

C. GRANULES AND PELLETS

Granules and pellets are physically stable, particulate compositions containing the active ingedients adhering to or distributed through a basic matrix of a coherent, inert carrier with macroscopic dimensions. A typical particle is about 1 to 2 millimeters in diameter. Surfactants are often present to aid in leaching of the active ingredients from the granule or pellet.

The carrier is preferably of mineral origin, and generally falls within one of two types. The first are porous, absorptive, performed granules, such as preformed and screened granular attapulgite or heat expanded, granular, screened vermiculite. On either of these, a solution of the active agent can be sprayed and will be absorbed at concentrations up to 25 weight percent of the total weight. The second, which are also suitable for pellets, are initially powdered kaolin clays, hydrated attapulgite, or bentonite clays in the form of sodium, calcium or magnesium bentonites. Water-soluble salts, such as sodium salts, may also be present to aid in the disintegration of granules or pellets in the presence of moisture. These ingredients are blended with the active components to give mixtures that are granulated or pelleted, followed by drying, to yield formulations with the active component distributed uniformly throughout the mass. Such granules and pellets can also be made with 25 to 30 weight percent active component, but more frequently a concentration of about 10 weight percent is desired for optimum distribution. The granular compositions of this invention are most useful in a size range of 15–30 mesh.

The surfactant is generally a common wetting agent of anionic or nonionic character. The most suitable wetting agents depend upon the type of granule used. When preformed granules are sprayed with active material in liquid form the most suitable wetting agents are nonionic, liquid wetters miscible with the solvent. These are compounds more generally known to the art as emulsifiers, and comprise alkylaryl polyether alcohols, alkyl polyether alcohols, polyoxyethylene sorbitan fatty acid esters, polythylene glycol esters with fatty or rosin acids, fatty alkylol amide condensates, oil solution petroleum or vegetable oil sulfonates, or mixtures of these. Such agents will usually comprise up to about 5 weight percent of the total composition.

When the active ingredient is first mixed with a powdered carrier and subsequently granulated, or pelleted, liquid nonionic wetters can still be used, but it is usually preferable to incorporate at the mixing stage one of the solid, powdered anionic wetting agents such as those previously listed for the wettable powders. Such agents will comprise from about 0 to 2 weight percent of the total composition.

Thus, the preferred granular or pelleted formulations of this invention comprise about 5 to 30 weight percent active material, about 0 to 5 weight percent wetting agent, and about 65 to 95 weight percent inert material carrier, as these terms are used herein.

D. MIRCOCAPSULES

Microcapsules consist of fuly enclosed droplets or granules containing the active materials, in which the enclosing material is an inert porous membrane, arranged to allow escape of the enclosed materials to the surrounding medium at controlled rates over a specified period. Microcapsules are particularly useful in the present invention since the organophosphorus compounds of the herbicide composition are liquid.

Encapsulated droplets are typically about 1 to 50 microns in diameter. The enclosed liquid typically constitutes about 50 to 95% of the weight of the entire capsule, and may contain a small amount of solvent in addition to the active materials.

Encapsulated granules are characterized by porous membranes sealing the openings of the granule carrier pores, trapping the liquid containing the active components inside for controlled release. A typical granule size ranges from 1 millimeter to 1 centimeter in diameter. In agricultural usage, the granule size is generally about 1 to 2 millimeters in diameter. Granules formed by extrusion, agglomeration, or prilling, are useful in the present invention as well s materials in their naturaly occurring form. Examples of such carriers are vermiculite, sintered clay granules, kaolin, attapulgite clay, sawdust, and granular carbon.

Useful encapsulating materials include natural and synthetic rubbers, cellulosic materials, styrene-butadiene copolymers, polyacrylonitriles, polyacrylates, polyesters, polyamides, poylurethanes, and starch xanthates.

E. INJECTION WITH ANHYDROUS AMMONIA

The herbicidal compositions of the instant invention comprising a thiocarbamate herbicide, organophosphorus extender and optionally an antidote can be applied to the soil by in-line injection with anhydrous ammonia. For pre-emergence soil injection applications of anhydrous ammonia, on conservation or conventional tilled acreage, the herbicidal composition of the instant invention can be introduced into the anhydrous line using a metering pump which offers a constant rate of the output per acre independent of the anhydrous ammonia output rate. The herbicidal composition discharge hose can tee into the ammonia discharge line between the meter and the manifold. Injection depth can be from 4 to 5 inches. The herbicidal compositions can also be injected with anhydrous ammonia in no-till situations.

Other herbicide products can be surface applied and incorporated at the same time the herbicidal compositions of the instant invention and anhydrous ammonia are injected, or post-emergent applications can be used.

F. IN GENERAL

Many of the above formulations can be prepred as a package containing both the thiocarbamate herbicide and the organophosphorus extender together with the other ingredients of the formulation (diluents, emulsifiers, surfactants, etc.). The formulations can also be prepred by a tank mix method, in which the ingredients are obtained separately and combined at the grower site. The herbicide and extender may both be used in the same type of formulation or a different formulation maybe used for each, e.g., the herbicide may be in microcapsule form while the extender may be an emulsifiable concentrate, or vice versa.

As a further alternative, the herbicide and extender can be applied sequentially, with either being applied first. This is a less preferred method, however, since more effective results are obtained with simultaneous application.

In general, any conventional method of application can be used. The locus of application can be soil, sees, seedlings, or the actual plants, as well as flooded fields. Soil application is preferred. Dusts and liquid compositions can be applied by the use of powder dusters, boom and hand sprayers, and spray dusters. The compositions can also be applied from airplanes as dusts or sprays because they are effective in very low dosages. In order to modify or control the growth of germinating seeds or emerging seedlings, as a typical example, the dust and liquid compositions are applied to the soil according to conventional methods and are distributed in the soil to a depth of at least one-half inch below the soil surface. It is not necessary that the phytotoxic compostions be admixed with the soil particles. Instead, these compositions can be applied merely by spraying or sprinkling the surface of the soil. The phytotoxic compositions of this invention can also be applied by additionn to irrigation water supplied to the field to be treated. This method of application permits the penetration of the compositions into the soil as the water is absorbed therein. Dust compositions, granular compositions or liquid formulations applied to the surface of the soil can be distributed below the surfacae of the soil by conventional means such as discing, dragging or mixing operations.

The herbicide/extender compositions can also be applied to the soil through irrigation systems. According to this technique, the compositions are added directly to irrigation water immediately prior to irrigation of the field. This technique is applicable in all geographical areas regardless of rainfall, since it permits supplementation of the natural rainfall at critical stages of plant growth. In a typical application, the concentration of the herbicide/extender composition in the irrigation water will range from about 10 to 150 parts per million by weight. The irrigation water can be applied by the use of sprinkler systems, surface furrows, or flooding. Such application is most effectively done before the weeds germinate, either early in the spring prior to germination or within two days after cultivation of the field.

The compositions of this invention can also contain further additaments, such as fertilizers, insecticides, or other herbicides. Suitable pesticides include 2,4-dichlorophenoxyacetic acids, 2,4,5-trichlorophenoxyacetic acid, 2-methyl-4-chlorophenoxyacetic acid, and the salts, esters and amides thereof; triazine derivatives, such as 2,4-bis(3-methoxypropylamino)-6-methyl-thio-s-triazine, 2-chloro-4-ethylamino-6-isopropylamino-s-triazine, 2-ethylamino-4-isopropylamino-6-methylmercapto-s-triazine; urea derivatives such as 3-(3,4-dichlorophenyl)-1,1dimethyl urea; acetamides such as N,N-diallyl-α-chloroacetamide, N-(α-chloroacetyl) hexamethyleneimine, and N,N-diethyl-α-bromoacetamide; and benzoic acids such a 3-amino-2,5-dichlorobenzoic acid. Fertilizers useful in combination with the active ingredients include ammonium nitrate, urea, and superphosphate. Other useful additaments include materials in which plant organisms take root and grow, such as compost, manure, humus, sand and the like.

The amount of composition of the present invention which constitutes a herbicidally effective amount depends upon the nature of the seeds or plants to be controlled. The rate of application of active ingredient varies from about 0.01 to about 50 pounds per acre, preferably about 0.1 to about 25 pounds per acre with the actual amount used depending on the overall cost and the desired results. It sill be readily apparent to one skilled in the art that compositions exhibiting lower herbicidal activity will require a higher dosage rate for the same degree of control than more active compounds.

What is claimed is:

1. An herbicidal composition comprising
   (a) an herbicidally effective amount of a thiolcarbamate having the formula

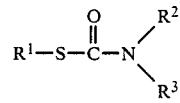

in which
$R^1$ is $C_1$–$C_6$ alkyl,
$R^2$ is $C_1$–$C_6$ alkyl,
$R^3$ is $C_1$–$C_6$ alkyl or cyclohexyl; and
   (b) an alkyl thiolcarbamate herbicide soil-life-extending non-phytotoxic amount of an organophosphorus compound having the formula

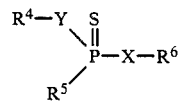

in which
Y is oxygen or sulfur;
$R^4$ is $C_1$–$C_6$ alkyl, optionally substituted with halo, or is $C_3$–$C_6$ alkenyl optionally substituted with cyano;
$R^5$ is $C_1$–$C_4$ alkyl, straight-chain $C_1$–$C_6$ alkoxy or $C_1$–$C_4$ alkylthio other than tertiary butylthio;
$R^6$ is $C_1$–$C_4$ alkyl substituted with one $C_1$–$C_3$ alkylthio group; $C_5$–$C_7$ cycloalkyl; $C_1$–$C_4$ alkylimino optionally substituted with one, two or three halogen atoms; phenyl optionally substituted with nitro, ortho-nitro and halo, $C_1$–$C_3$ alkylsulfinyl, α-pentynyl, or trifluoromethyl; benzyl optionally substituted with halo; or is -($R^7$)-φ in which
$R^7$ is $C_1$–$C_4$ alkylene substituted with either cyano or with one, two or three halogen atoms; and φ is phenyl substituted with halo when $R_7$ is substituted with cyano but is phenylthio subsituted with halo with $R_7$ is substituted with one, two or three halogen atoms;

X is oxygen or sulfur; with the provisos that:
when $R^4$ is $C_1$–$C_6$ alkyl, $R^4$ is other than tertiary butyl;
when $R^6$ is $C_5$–$C_7$ cycloalkyl, substituted or unsubstituted phenyl, or substituted or unsubstituted benzyl, then X must be oxygen;
when $R^4$ is allyl, Y is oxygen, and $R^6$ is para-nitrophenyl, then $R^5$ is other than methyl; and
when $R^4$ is methyl and $R^6$ is phenyl, then $R^5$ is other than $C_1$–$C_4$ alkylthio or ethoxy.

2. An herbicidal composition according to claim 1 wherein
$R^4$ is $C_1$–$C_6$ alkyl, other than tertiary butyl, optionally substituted with halo;
$R^5$ is ethyl, straight-chain $C_1$–$C_4$ alkoxy, or $C_1$–$C_4$ alkylthio other than tertiary butylthio;
$R^6$ is $C_5$–$C_7$ cycloalkyl, benzyl or phenyl optionally substituted with either halo, or ortho-nitro and halo; and
X is oxygen.

3. An herbicidal composition according to claim 1 wherein
$R^4$ is ethyl, n-propyl, or n-butyl;
$R^5$ is methoxy, ethoxy, n-propoxy, ethylthio, or n-propylthio;
$R^6$ is $C_5$–$C_7$ cycloalkyl, benzyl or phenyl optionally substituted with halo;
X is oxygen; with the provision that wherein Y is sulfur, $R^4$ is ethyl, n-propyl or n-butyl and $R^6$ is phenyl, $R_5$ is other than methoxy.

4. An herbicidal composition according to claim 1 wherein the organophosphorus compound is O,O-diethyl-O-phenyl phosphorothioate.

5. An herbicidal composition according to claim 4 wherein the thiocarbamatae is S-ethyl N,N-di-n-propyl thiocarbamate.

6. An herbicidal composition according to claim 4 wherein the thiocarbamate is S-ethyl N,N-diisobutyl thiocarbamate.

7. An herbicidal composition according to claim 4 wherein the thiocarbamate is S-propyl N,N-dipropyl thocarbamate.

8. An herbicidal composition according to claim 1 wherein the organophosphorous compound is O,O-diethyl-O-benzyl phosphorothioate.

9. An herbicidal composition according to claim 1 wherein the organophosphorus compound is O-ethyl-O-phenyl-S-n-propyl phosphorodithioate.

10. An herbicidal composition according to claim 1 wherein the organophosphorus compound is O-ethyl-S-ethyl-O-phenyl phosphorothioate.

11. An herbicidal composition according to claim 1 wherein the organophosphorus compound is O-ethyl-O-phenyl-S-n-buty phosphorothioate.

12. An herbicidal composition according to claim 1 wherein the weight ratio of said thiocarbamate to said organophosphorus compound is from about 1:1 to about 25:1.

13. An herbicidal composition according to claim 1 wherein the weight ratio of said thiocarbamate to said organophosphorus compound is from about 1:1 to about 15:1.

14. A method of controlling undesirable vegetation comprising applying to the locus where control is desired both
(a) an herbicidally effective amount of a thiolcarbamate having the formula

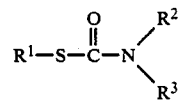

in which
$R^1$ is $C_1$–$C_6$ alkyl,
$R^2$ is $C_1$–$C_6$ alkyl
$R^3$ is $C_1$–$C_6$ alkyl or cyclohexyl; and
(b) an alkyl thiolcarbamatae herbicide soil-life-extending non-phytotoxic amount of an organophosphorus compound having the formula

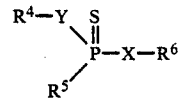

in which
Y is oxyen or sulfur;
$R^4$ is $C_1$–$C_6$ alkyl, optionally substituted with halo, or is $C_3$–$C_6$ alkenyl optionally substituted with cyano;
$R^5$ is $C_1$–$C_4$ alkyl, straight-chain $C_1$–$C_6$ alkoxy or $C_1$–$C_4$ alkylthio other than tertiary butylthio;
$R^6$ is $C_1$–$C_4$ alkyl substituted with one $C_1$–$C_3$ alkylthio group; $C_5$–$C_7$ cycloalkyl; $C_1$–$C_4$ alkylimino optionally substituted with one, two or three halogen atoms; phenyl optionally substituted with nitro, ortho-nitro and halo, $C_1$–$C_3$ alkylsulfinyl, $\alpha$-pentynyl, or trifluoromethyl; benzyl optionally substituted with halo; or is -($R^7$)-$\phi$ in which
$R^7$ is $C_1$–$C_4$ alkylene substituted with either cyano or with one, two or three halogen atoms; and $\phi$ is phenyl substituted with halo when $R_7$ is substituted with cyano but is phenylthio substituted with halo when $R_7$ is substituted with one, two or three halogen atoms;
X is oxygen or sulfur; with the provisos that:
when $R^4$ is $C_1$–$C_6$ alkyl, $R^4$ is other than teritary butyl;
when $R^6$ is $C_5$–$C_7$ cycloalkyl, substituted or unsubstituted phenyl, or substituted or unsubstituted benzyl, then X must be oxygen;
when $R^4$ is allyl, Y is oxygen, and $R^6$ is para-nitrophenyl, then $R^5$ is other than methyl; and
when $R^4$ is methyl and $R^6$ is phenyl, then $R^5$ is other than $C_1$–$C_4$ alkylthio or ethoxy.

* * * * *